United States Patent
Katsunuma

(10) Patent No.: US 10,195,339 B2
(45) Date of Patent: Feb. 5, 2019

(54) FLUIDIC PUMP

(71) Applicant: TERUMO KABUSHIKI KAISHA, Tokyo (JP)

(72) Inventor: Takayuki Katsunuma, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 369 days.

(21) Appl. No.: 14/663,224

(22) Filed: Mar. 19, 2015

(65) Prior Publication Data
US 2015/0265763 A1    Sep. 24, 2015

(30) Foreign Application Priority Data
Mar. 20, 2014  (JP) .................. 2014-058603

(51) Int. Cl.
| | | |
|---|---|---|
| *A61M 5/142* | (2006.01) | |
| *A61M 5/145* | (2006.01) | |
| *G06F 19/00* | (2018.01) | |
| *G16H 40/40* | (2018.01) | |
| *A61M 5/172* | (2006.01) | |
| *A61M 5/31* | (2006.01) | |

(52) U.S. Cl.
CPC .......... *A61M 5/142* (2013.01); *A61M 5/1456* (2013.01); *G06F 19/3468* (2013.01);
(Continued)

(58) Field of Classification Search
CPC ........ A61M 5/142; A61M 2005/14208; A61M 2005/3125; A61M 2005/1492;
(Continued)

(56) References Cited

U.S. PATENT DOCUMENTS

| | | | | |
|---|---|---|---|---|
| 4,587,967 A | * | 5/1986 | Chu ............... | A61M 16/12 128/204.21 |
| 5,694,926 A | * | 12/1997 | DeVries ........... | A61M 16/125 128/204.21 |

(Continued)

FOREIGN PATENT DOCUMENTS

| | | |
|---|---|---|
| JP | 11-507860 | 7/1999 |
| JP | 2005-13413 | 1/2005 |

(Continued)

OTHER PUBLICATIONS

Official Action (English machine translation) for Japanese Patent Application No. 2014-058603, dated Nov. 17, 2017, 4 pages.

*Primary Examiner* — Bradley J Osinski
*Assistant Examiner* — Nilay Shah
(74) *Attorney, Agent, or Firm* — Jason H. Vick; Sheridan Ross, PC

(57) ABSTRACT

Provided is a liquid delivering pump which can determine whether the pump is suitable for use, while in a standby state, and thus, the pump can be efficiently managed and utilized. A liquid delivering pump which delivers a drug to the inside of a living body includes a storage unit that stores a drug library, a starting state switching unit that switches a starting state of the liquid delivering pump between a liquid deliverable state and a standby state, and a display unit that displays various types of information related to the liquid delivering pump. The display unit displays specification information which specifies the drug library stored in the storage unit, while in the standby state.

10 Claims, 16 Drawing Sheets

(52) U.S. Cl.
CPC ............ *G16H 40/40* (2018.01); *A61M 5/172* (2013.01); *A61M 2005/14208* (2013.01); *A61M 2005/3125* (2013.01); *A61M 2205/14* (2013.01); *A61M 2205/18* (2013.01); *A61M 2205/332* (2013.01); *A61M 2205/502* (2013.01); *A61M 2205/52* (2013.01); *G06F 19/326* (2013.01)

(58) Field of Classification Search
CPC ............ A61M 5/172; A61M 5/31546; A61M 2205/502; G06F 19/3412; G06F 19/3468; G06F 19/326
See application file for complete search history.

(56) References Cited

U.S. PATENT DOCUMENTS

| | | | | |
|---|---|---|---|---|
| 5,782,805 | A | * | 7/1998 | Meinzer ............ A61M 5/172 604/131 |
| 2005/0177096 | A1 | * | 8/2005 | Bollish ............ A61B 5/02055 604/65 |
| 2007/0213598 | A1 | * | 9/2007 | Howard ............ A61M 5/142 600/300 |
| 2008/0125700 | A1 | * | 5/2008 | Moberg ............ A61M 5/14244 604/67 |
| 2011/0112696 | A1 | * | 5/2011 | Yodfat ............ G05D 7/0676 700/283 |
| 2011/0320049 | A1 | * | 12/2011 | Chossat ............ G06F 19/3468 700/283 |

FOREIGN PATENT DOCUMENTS

| | | |
|---|---|---|
| JP | 2005-013413 A | 1/2005 |
| JP | 2011-507860 | 3/2011 |
| JP | 2011-521744 | 7/2011 |
| JP | 2012-179099 | 9/2012 |
| WO | WO 97/37704 | 10/1997 |
| WO | WO 2013/069305 | 5/2013 |

\* cited by examiner

FLUIDIC PUMP

CROSS REFERENCE TO RELATED APPLICATIONS

This application claims priority to JP2014-058603, filed Mar. 20, 2014, entitled "Liquid Delivery Pump", which is incorporated herein by reference in its entirety and for all purposes.

TECHNICAL FIELD

The embodiments herein generally relate to a liquid delivering pump which is used for delivering a drug to the inside of a patient.

BACKGROUND

There is provided a medical pump as an apparatus which performs delivering treatment of drug, for example, anti-cancer drugs, anesthetics, chemotherapeutics, blood preparations, nutrients and the like. The medical pump can be used in an intensive care unit (ICU) or the like. As a medical pump, which high precisely delivers liquid for a long period of time, the pump can have a syringe pump and/or an infusion pump, for example.

For a drug which is delivered by using a medical pump, a proper value or an upper limit value for a flow rate of liquid to be delivered or a proper value or an upper limit value for an infusion rate of a drug is prescribed for each type of drug. When delivering the drug by using a medical pump, various parameters such as the proper value or the upper limit value thereof need to be properly set to the medical pump. If the various parameters are not properly set, a desired effect may not be achieved.

To prevent various parameters from being erroneously set, there is a known method of using a drug library. The drug library is a file in which various parameters prescribed for each type of drug are recorded. As the drug library is stored in a medical pump, setting of various parameters can be simplified. Specifically, when using a medical pump, various parameters are automatically set to the medical pump by selecting a type of drug which is set to the medical pump as the drug to be delivered from types of drugs recorded in the drug library.

SUMMARY

Technical Problem

In a case of a medical pump storing a drug library, to discriminate whether or not the pump is suitable for use, there is a need to check at least whether or not information of the stored drug library is appropriate. If the information of the stored drug library is not appropriate, for example, various parameters such as a proper value or an upper limit value for a flow rate of liquid to be delivered or a proper value or an upper limit value for an infusion rate of drug may not be appropriately set, the pump should not be used. Information about a drug suitable for use may not be recorded in the drug library. In a medical pump in the related art, checking whether or not the information of the stored drug library is appropriate cannot be performed unless the medical pump is in an activated state.

In general, medical pumps are kept and managed in a medical engineer (ME) room, and the like, when not in use. In this case, to use the kept medical pump for delivering liquid, there is a need to select a pump suitable for use from a plurality of the kept medical pumps and to carry the pump to a site used for delivering liquid. However, the medical pumps kept and managed in the ME room and the like are mostly connected to external power sources to be in a state of charge. Accordingly, to perform the aforementioned checking related to determining whether or not the pump is suitable for use, there is a need to activate the medical pump once when in the state of charge. A certain period of time is required for activating the pump. Therefore, the medical pump cannot be promptly carried to the site used for delivering liquid, thereby being a hindrance to efficient utilization.

To avoid the aforementioned problem, a management method has been created, for a medical pump, performed by attaching a label stating information, which specifies a drug library stored in the medical pump, to the medical pump. However, the label needs to be replaced every time the stored drug library is updated. Thus, the medical pump cannot be efficiently managed.

The embodiments herein address the above-described problems, thereby providing a liquid delivering pump which can discriminate whether or not the pump is suitable for use while in a standby state so that the pump can be efficiently managed and utilized.

Solution to the Problem

To achieve the above-described object, a liquid delivering pump, which delivers drug to the inside of a living body, includes a storage unit that stores a drug library, a starting state switching unit that switches a starting state of the liquid delivering pump between a liquid deliverable state and a standby state, and a display unit that displays various types of information related to the liquid delivering pump. The display unit displays specification information, which specifies the drug library stored in the storage unit, while in the standby state.

Advantageous Effects

Specification information which specifies a drug library stored in a storage unit can be displayed while in a standby state. Accordingly, it is possible to discriminate whether or not the pump is suitable for use, while in the standby state. Therefore, it is possible to provide a liquid delivering pump which can be efficiently managed and utilized.

The specification information which specifies a drug library may be configured to include updated identification information of the drug library. Accordingly, it is possible to discriminate whether or not a drug library stored in the storage unit is appropriately updated, while in the standby state. Therefore, according to the configuration thereof, it is possible to discriminate whether or not the pump can deliver liquid, while in the standby state, based on appropriate information, thereby improving convenience.

The specification information which specifies a drug library may be configured to include information which specifies a profile applied to the liquid delivering pump. According to the configuration, it is possible to determine whether information of drug suitability for use is recorded in a drug library stored in the storage unit, while in the standby state. It is also possible to simultaneously determine whether a type of drug, suitable for use, can be promptly selected by the pump, while in the standby state, thereby further improving convenience.

Profile IDs may be respectively set so as to cause a plurality of the profiles stored in the storage unit to be identifiable. The display unit may be configured to display a visually identifiable icon replacing the profile ID set to the applied profile when displaying the information which specifies an applied profile applied to the liquid delivering pump as the specification information which specifies a drug library. According to the configuration, it is possible to visually perform determining whether the pump is suitable for use. Therefore, the time taken for determination is reduced, thereby improving convenience. Erroneous identification is prevented during determination, thereby improving safety.

The display unit may be configured so as to vary a display state at the time of displaying the specification information, which specifies a drug library, in accordance with the applied profile. According to the configuration, the applied profile can be easily identified. Therefore, it is possible to decrease erroneous identification at the time of discriminating whether or not a profile suitable for use is applied, thereby further improving convenience and safety.

The display unit may be configured so as to vary the display state at the time of displaying the specification information, which specifies a drug library, in accordance with an elapsed time from an update of the drug library. According to the configuration, an elapsed time from an update of a drug library stored in the storage unit can be easily identified. Therefore, it is possible to decrease erroneous identification at the time of discriminating whether or not the drug library stored in the storage unit is appropriately updated, thereby further improving convenience and safety.

The storage unit may be configured so as to store a periodic inspection time. The display unit may be configured so as to display information which notifies a user of an arrival state of the periodic inspection time, while in the standby state. According to the configuration, it is possible to discriminate whether or not periodical inspection is appropriately performed, while in the standby state, and thus, a pump can be more efficiently managed and utilized.

The configuration may include a shock detection unit which detects whether or not the pump was subjected to a shock. The display unit may be configured to display information which notifies a user of whether or not a shock was detected by the shock detection unit, while in the standby state. According to the configuration, it is possible to discriminate whether or not a shock was detected, while in the standby state, and thus, a pump can be more efficiently managed and utilized.

The display unit may be configured to include a power mode switching unit, which switches a power mode between a normal power mode and an energy-saving power mode in which less power is consumed than the normal power mode, and the specification information is displayed so as to be visually recognizable when displaying the specification information which specifies a drug library, while in the standby state. The power mode switching unit may be configured to switch the power mode from the normal power mode to the energy-saving power mode when no operation is performed with respect to the liquid delivering pump for a predetermined time while in the normal power mode. According to the configuration, it is possible to decrease power consumption when displaying information necessary to discriminate whether or not the pump is suitable for use, while in the standby state. Thus, a pump can be more efficiently managed and utilized.

The display unit may be configured to display a reception screen, which receives selection of a type of drug to be delivered, while in a liquid deliverable state and to display the specification information which specifies a drug library on the reception screen. According to the configuration, it is possible to discriminate whether or not the pump is suitable for use when selecting a type of drug to be delivered, while in the liquid deliverable state. Therefore, it is possible to prevent a pump, not suitable for use, from being used, thereby improving safety.

DETAILED DESCRIPTION

Hereinafter, embodiments will be described with reference to the drawings. Note that, for convenience of description, dimensional ratios of the drawings may be exaggerated, thereby being different from the actual dimensional ratios.

Figure 1:
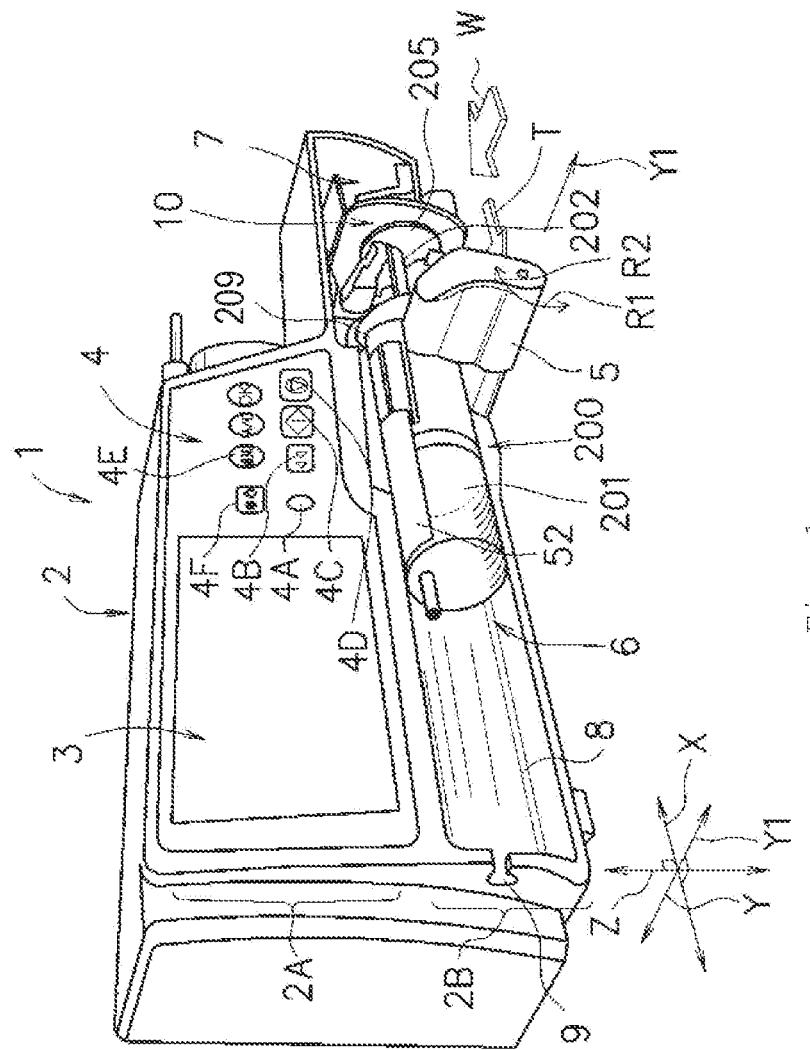
FIG. 1 is a schematic perspective view for illustrating an embodiment of a syringe pump.
Figure 2:
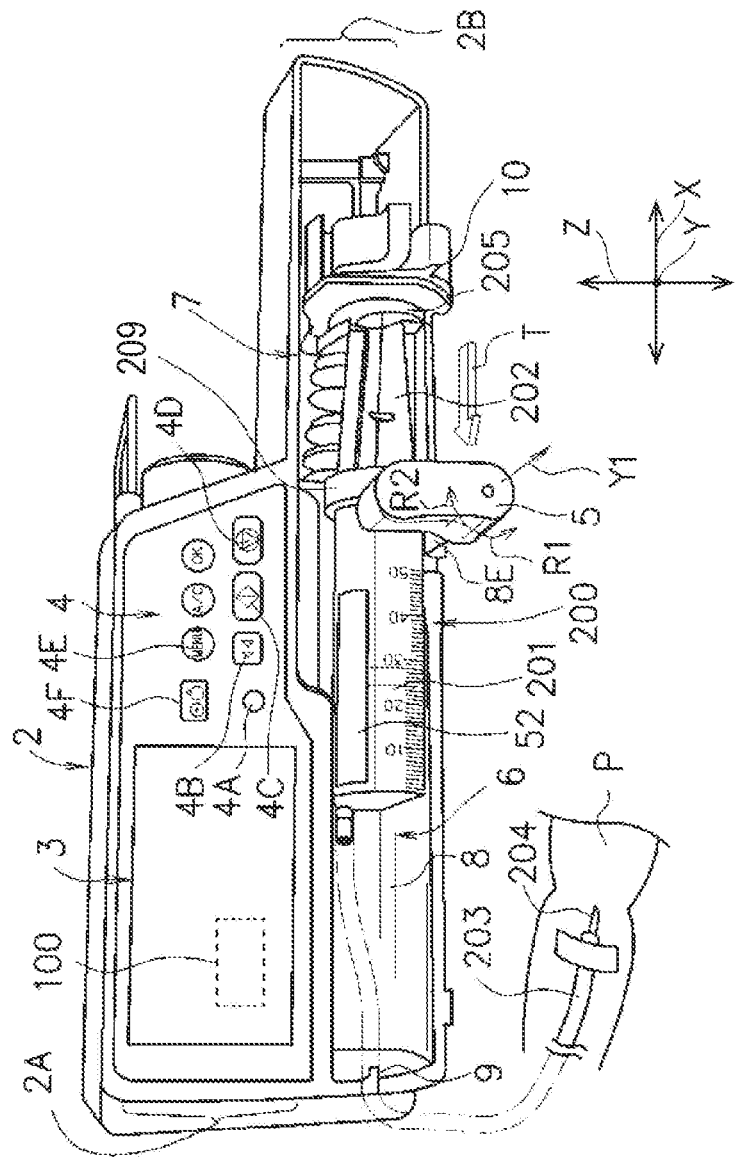
FIG. 2 is a schematic front view for illustrating the syringe pump.

As illustrated in FIGS. 1 and 2, a syringe pump 1 is a liquid delivering pump which is used in an intensive care unit (ICU), or the like, to deliver one or more drug(s) to the inside of a patient for a long period of time. The syringe pump 1 can deliver various types of drugs including intravenous anesthetics, and the like, to the inside of a patient. As applicable, intravenous anesthetics, propofol, midazolam, remifentanil and the like are examples of drugs that may be delivered.

Hereinafter, an apparatus configuration of the syringe pump 1 will be described in detail.

As illustrated in FIGS. 1 and 2, the syringe pump 1 precisely delivers drug(s), inside a syringe main body 201 to a patient P through a tube 203 and an indwelling needle 204 by pressing a syringe plunger 202 of a syringe 200 which is filled with a drug, as a drug container, in a T-direction. In this case, the syringe main body 201 of the syringe 200 is coupled to the syringe pump 1 so as not to be moved by a clamp 5.

The syringe pump 1 has a main body cover 2.

The main body cover 2 is integrally molded of a molding resin material resistant to chemicals. Therefore, the main body cover 2 has a splash-proof treatment structure. On account of the splash-proof treatment structure, it is possible to prevent the drug, or the like from penetrating into the syringe pump 1 even in a case where the drug is splashed over the syringe pump 1. The splash-proof treatment structure is provided because there may be a case where a drug inside the syringe main body 201 is spilt or antiseptic solutions or the like used in the vicinity thereof may be splashed.

As illustrated in FIGS. 1 and 2, the main body cover 2 has an upper portion 2A and a lower portion 2B.

A display unit 3 and an operation panel section 4 are arranged in the upper portion 2A.

A syringe setting portion 6 and a syringe plunger drive unit 7 which presses the syringe plunger 202 are arranged in the lower portion 2B.

The display unit 3 is an image display device capable of color display. For example, the display unit 3 can be formed with a color liquid crystal display device. The display unit 3 can display information not only by notation in English but also by notation in multiple foreign languages as necessary. The display unit 3 is arranged at a position to the upper left in the upper portion 2A of the main body cover 2, that is, on the upper side of the syringe setting portion 6 and the syringe plunger drive unit 7.

The operation panel section 4 is arranged on the right side of the display unit 3 in the upper portion of the main body cover 2. A power ON/OFF button 4F, a motion indicator 4A, and operation buttons are arranged in an operation panel section 4. FIGS. 1 and 2 show an example in which four operation buttons of a fast-forward switch button 4B, a start switch button 4C, a stop switch button 4D, and a menu selection button 4E are arranged as the minimum required operation buttons.

As illustrated in FIGS. 1 and 2, the syringe setting portion 6 and the syringe plunger drive unit 7 are arranged side by side along an X-direction. A syringe is selected from syringes 200, 300, and 400 which are different from one another in multiple types of size so as to be able to fit into the syringe setting portion 6 and to be detachably fixed thereto. The syringes 200, 300, and 400 will be described later with reference to FIG. 4.

As illustrated in FIGS. 1 and 2, the syringe setting portion 6 has an accommodation portion 8 which accommodates the syringe main body 201, and the clamp 5. The accommodation portion 8 is a concave portion having a substantially semicircular cross section so as to accommodate the syringe main body 201 and is formed along the X-direction. A tube fixing portion 9 is formed on a wall at an end portion of the accommodation portion 8 so as to detachably pinch the tube 203.

When detaching the syringe 200 from the syringe setting portion 6 by operating the clamp 5, the clamp 5 is pulled out against a force of a spring (not illustrated) in a Y1-direction (a front direction) and is turned by 90 degrees in an R1-direction so that the syringe main body 201, fixed by the clamp 5, can be released and detached from the accommodation portion 8. When attaching the syringe 200 to the syringe setting portion 6, by operating the clamp 5, the clamp 5 is pulled out against a force of a spring (not illustrated) in the Y1-direction, is turned by 90 degrees in an R2-direction, and is returned in a W-direction by a force of the spring so that the syringe main body 201 can be accommodated in the accommodation portion 8 and be fixed by the clamp 5. To allow the clamp 5 to fix syringes respectively having capacities of 2.5 mL, 5 mL, 10 mL, 20 mL, 30 mL, and 50 mL, a right end portion 8E of the accommodation portion 8 in the syringe setting portion 6 is partially formed to have a notch portion.

When the syringe main body 201 is accommodated in the accommodation portion 8 and is fixed thereto, the syringe plunger 202 is arranged in the syringe plunger drive unit 7. The syringe plunger drive unit 7 has a slider 10. The slider 10 gradually presses a plunger flange 205 of the syringe plunger 202 relatively along a T-direction with respect to the syringe main body 201, in response to a command from a control unit 100 illustrated in FIGS. 2 and 5.

Note that, the X-direction, the Y-direction, and a Z-direction in FIGS. 1 and 2 are orthogonal to one another. The Z-direction is a vertical direction.

Figure 3:
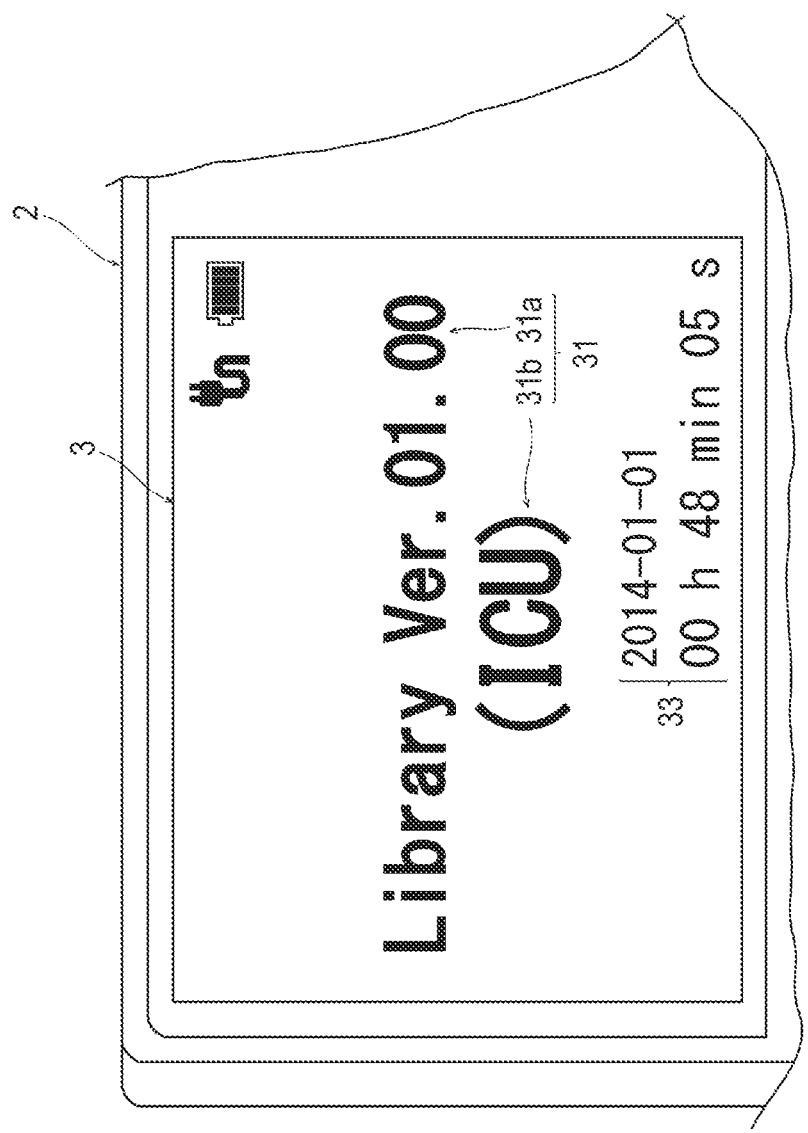
FIG. 3 is a schematic front view for illustrating a display unit of the syringe pump.

FIG. 3 illustrates a display example of the display unit 3. The display example of the display unit 3 is an example, and thus, the embodiment is not particularly limited thereto.

Figure 4:
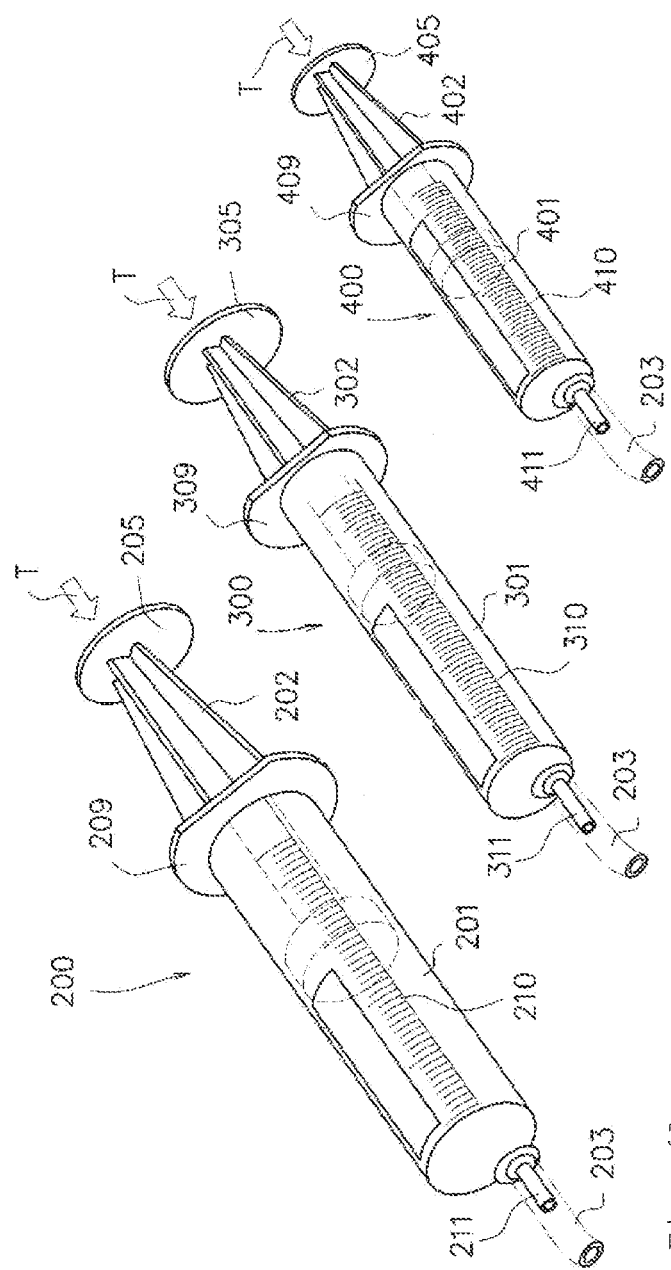
FIGS. 4(A) to 4(C) are schematic perspective views for illustrating syringes which are applied to the syringe pump.

FIG. 4 is a perspective view illustrating examples of the above-described syringes in multiple types of size.

FIGS. 1 and 2 illustrate examples in which the syringe 200 having the largest capacity for drug is fixed.

As illustrated in FIG. 4(A), the syringe 200 having the largest capacity for a drug includes the syringe main body 201 and the syringe plunger 202. The syringe main body 201 has a main body flange 209, and the syringe plunger 202 has the plunger flange 205. A scale 210 for the drug is formed in the syringe main body 201. One end portion of a flexible tube 203 is detachably connected to an outlet portion 211 of the syringe main body 201.

As illustrated in FIG. 4(B), the syringe 300 having an intermediate capacity for the drug includes a syringe main body 301 and a syringe plunger 302. The syringe main body 301 has a main body flange 309, and the syringe plunger 302 has a plunger flange 305. A scale 310 for the drug is formed in the syringe main body 301. The one end portion of the flexible tube 203 is detachably connected to an outlet portion 311 of the syringe main body 301.

As illustrated in FIG. 4(C), the syringe 400 having the smallest capacity for drug includes a syringe main body 401 and a syringe plunger 402. The syringe main body 401 has a main body flange 409, and the syringe plunger 402 has a plunger flange 405. A scale 410 for drug is formed in the syringe main body 401. The one end portion of the flexible tube 203 is detachably connected to an outlet portion 411 of the syringe main body 401.

For example, the syringe 200 illustrated in FIG. 4(A) has a capacity of 50 mL for the drug. For example, the syringe 300 illustrated in FIG. 4(B) has capacities of 10 mL, 20 mL, and 30 mL for the drug. For example, the syringe 400 illustrated in FIG. 4(C) has capacities of 2.5 mL and 5 mL for the drug. The syringes 300 and 400 can be used by being accommodated in the accommodation portion 8 and fixed thereto, similarly to the syringe 200 illustrated in FIGS. 1 and 2.

Subsequently, an example of an electrical configuration of the syringe pump 1 illustrated in FIGS. 1 and 2 will be described in detail with reference to FIG. 5.

Figure 5:
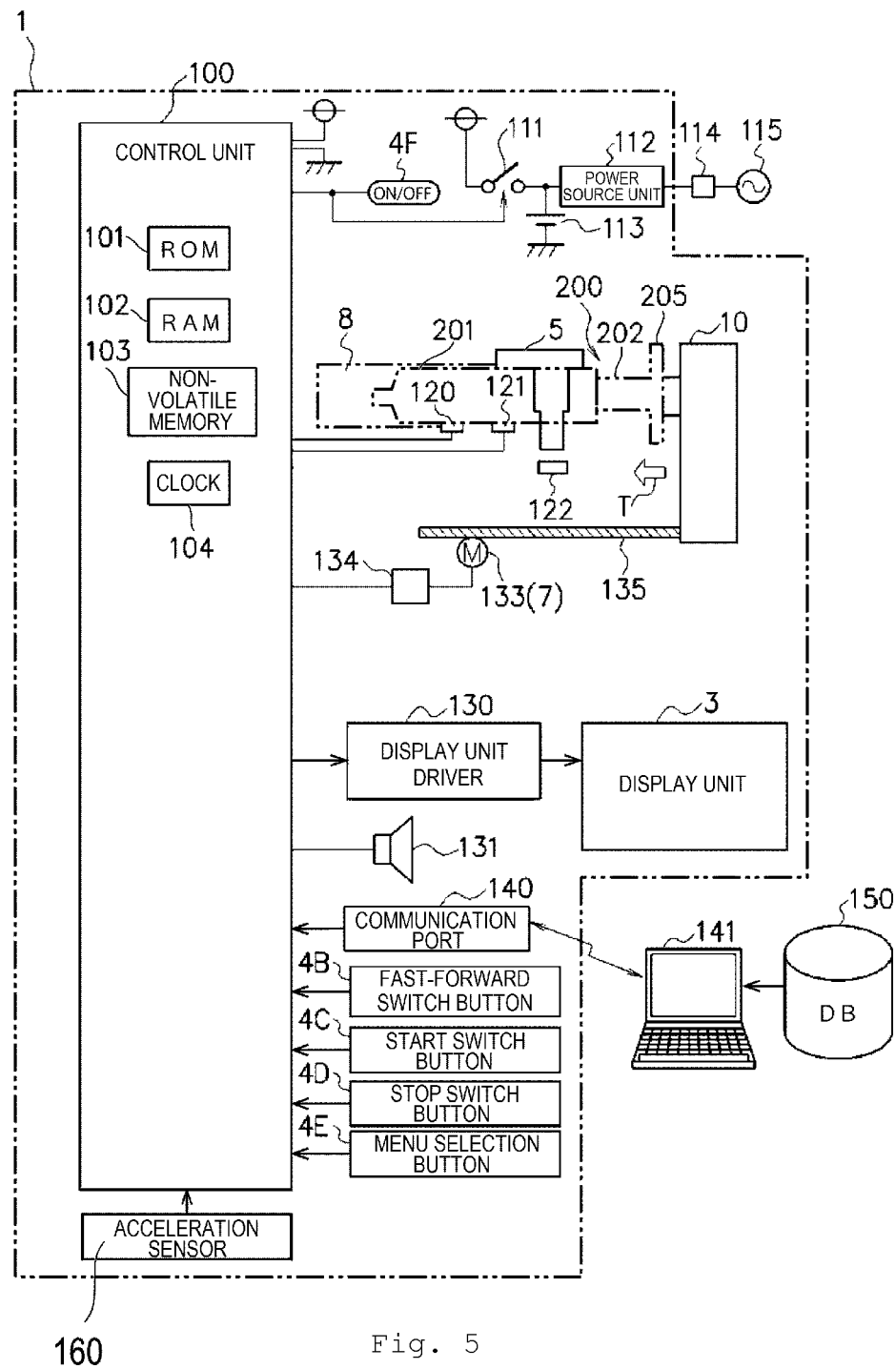
FIG. 5 is a schematic view for illustrating an electrical configuration of the syringe pump.

In FIG. 5, the syringe pump 1 has a control unit (a computer) 100 which performs judging and controlling of overall operations. The control unit 100 is, for example, a one-chip microcomputer and has a ROM (read only memory) 101, a RAM (random access memory) 102, a non-volatile memory 103, and a clock 104.

The clock 104 can correct a current time, can acquire the current time, can measure an elapsed time for predetermined liquid delivering, and can measure a reference time for controlling a speed of liquid delivering by performing predetermined operations, for example.

The power ON/OFF button 4F and a switch 111 are connected to the control unit 100 illustrated in FIG. 5.

As the power ON/OFF button 4F is pressed, a control signal for switching a starting state is input to the control unit 100.

The switch 111 allows a power source to be supplied to the control unit 100 from either a power source converter 112 or a rechargeable battery 113, a lithium-ion battery for example, by switching between the power source converter 112 and the rechargeable battery 113.

The power source converter 112 is connected to a commercial AC power source 115 through a power plug 114.

In FIG. 5, the fast-forward switch button 4B, the start switch button 4C, the stop switch button 4D, and the menu selection button 4E are electrically connected to the control unit 100. As the start switch button 4C is pressed, a control signal to start liquid delivering is input to the control unit 100. As the stop switch button 4D is pressed, a control signal to stop liquid delivering is input to the control unit 100.

In FIG. 5, a display unit driver 130 is electrically connected to the control unit 100. The display unit driver 130 drives the display unit 3 in response to a command from the control unit 100, thereby causing the display unit 3 to display various types of information.

In FIG. 5, a speaker 131 is electrically connected to the control unit 100. The speaker 131 notifies a user of various types of audio alarms in response to a command from the control unit 100.

In FIG. 5, a pair of detection switches 120 and 121 are arranged in the accommodation portion 8. The detection switches 120 and 121 detect whether or not the syringe main body 201 of the syringe 200 is properly arranged in the accommodation portion 8, thereby notifying the control unit 100 thereof.

A clamp sensor 122 detects a positional state of the clamp 5 and notifies the control unit 100 of whether or not the syringe main body 201 is securely clamped by the clamp 5.

As a motor 133 of the syringe plunger drive unit 7 is driven by a motor driver 134 in response to a command from the control unit 100, the motor 133 rotates a feed screw 135, thereby moving the slider 10 in the T-direction. In this manner, the slider 10 precisely delivers the drug, inside the syringe main body 201, illustrated in FIG. 2; to the patient P through the tube 203 and the indwelling needle 204 by pressing the syringe plunger 202 in the T-direction.

In FIG. 5, an acceleration sensor 160 is connected to the control unit 100. The acceleration sensor 160 measures acceleration applied to the syringe pump 1 and notifies the control unit 100 thereof.

The non-volatile memory 103 functions as a storage unit which stores a drug library that can be updated. For the drug, which is delivered by using the syringe pump 1, a proper value or an upper limit value for a flow rate of liquid to be delivered or a proper value or an upper limit value for an infusion rate of drug is prescribed for each type of the drug. When delivering the drug, the drug needs to be delivered in accordance with the various parameters, such as the proper value or the upper limit value. The drug library is a file in which various parameters prescribed in accordance with the type of drug are recorded.

A method of storing the drug library in the non-volatile memory 103 is not particularly limited. However, for example, the drug library can be stored through a communication port 140. In other words, as illustrated in FIG. 5, a computer 141 such as a desktop computer is connected to the control unit 100 through the communication port 140. The computer 141 is connected to drug database 150. The drug library is kept in the drug database 150. The drug library kept in the drug database 150 can be stored in the non-volatile memory 103 through the communication port 140 by operating the computer 141.

The drug library is updated in cases as described below. That is, the drug library is updated when adding a new type of drug and when updating, adding, and deleting information related to the types of drug which have already been stored in the library. The drug library, stored in the non-volatile memory 103, can be also updated by the method of using the communication port 140 and the computer 141 described above.

The control unit 100 controls the motor driver 134 so as to deliver liquid in accordance with the various parameters with reference to information of the drug library stored in the non-volatile memory 103.

To cause the control unit 100 to deliver the drug, with reference to the information of the drug library, the type of drug which fills the syringe main body 201 set to the syringe setting portion 6 needs to be selected from the types of drug(s) recorded in the drug library and input to the control unit 100 in advance.

The types of drug(s) amounting to thousands of types can be recorded in the drug library. Therefore, as the types of drug(s) recorded in the drug library increase, the time taken for selecting the type of drug, which fills the syringe main body 201, from the drug library increases. Here, there is a known method in which types of drug recorded in a drug library are narrowed in accordance with the purpose of use, and the result thereof is recorded in a file which is so-called a profile. The profile can be generated in multiple numbers in accordance with the purpose of use of the syringe pump 1. For example, the types of drug(s) which are likely to be used are selected and recorded in the profile for each medical treatment room, such as, an intensive care unit (ICU), a coronary care unit (CCU), a neonatal intensive care unit (NICU), a stroke care unit (SCU), and the like. The non-volatile memory 103 can store a plurality of the profiles, which may be periodically updated.

For example, the profile stored in the non-volatile memory 103 can be generated by operating the operation buttons of the operation panel section 4 in accordance with display contents of the display unit 3.

Figure 6A:
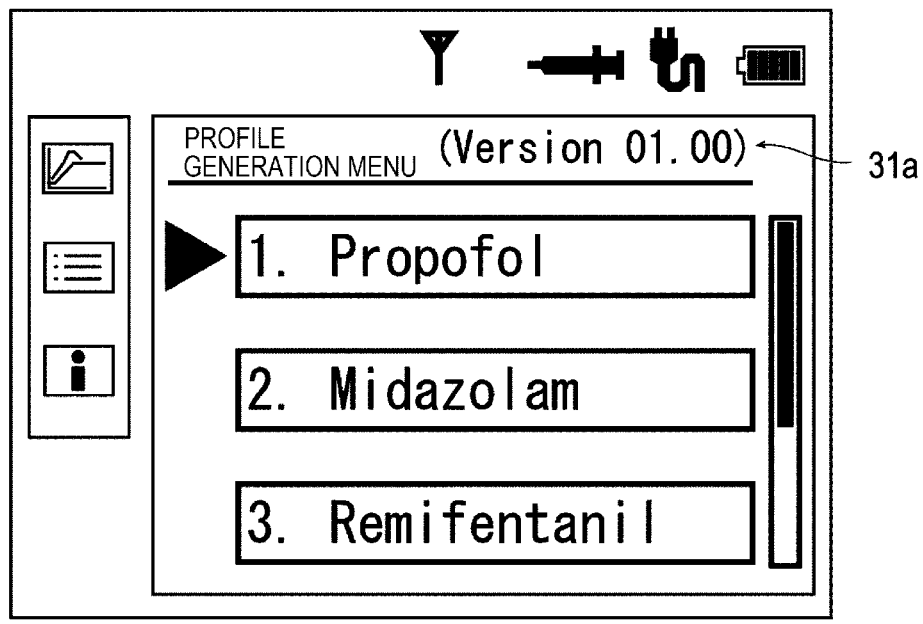
FIGS. 6(A) and 6(B) are other schematic front views for illustrating the display unit of the syringe pump, and the views illustrate display examples when generating a profile.
Figure 6B:
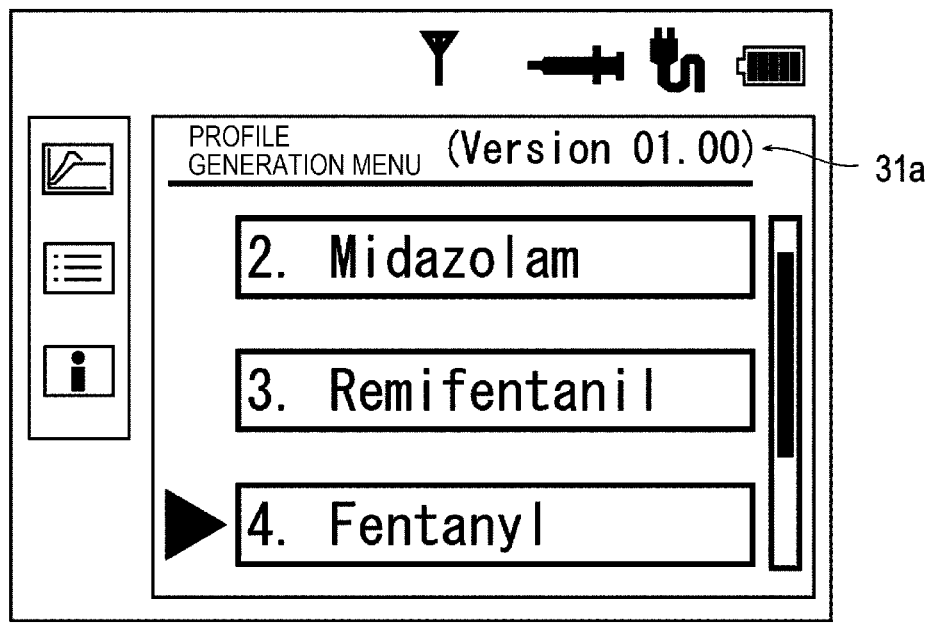

FIGS. 6(A) and 6(B) illustrate examples of the display contents of the display unit 3 at the time of generating the profile. The profile can be generated by operating the operation buttons of the operation panel section 4 in accordance with the examples of the display contents illustrated in FIGS. 6(A) and 6(B).

Specifically, as illustrated in FIGS. 6(A) and 6(B), the display unit 3 exhibits a scroll-type display of the types of drug(s) stored in the drug library. The operation buttons, of the operation panel section 4, are operated to select a suitable type of drug from the types of drug(s) displayed on the display unit 3 in accordance with the purpose of use, or the like. The selected type of drug is stored in the non-volatile memory 103 as the profile.

It is also possible to generate the profile so as to be recorded in the drug library by using the computer 141. In this case, as the drug library is stored in the non-volatile memory 103, the profile is simultaneously stored in the non-volatile memory 103.

The profile stored in the non-volatile memory 103 can be set to have a name. The names can be set as, for example, Intensive Care Unit (ICU), Coronary Care Unit (CCU), Neonatal Intensive Care Unit (NICU), and Stroke Care Unit (SCU). The name of a hospital ward can be set as the profile name.

The profile is updated in cases as described below. That is, the profile is updated when adding a new type of drug and when deleting the types of drug(s) which have already been recorded. Similarly to the method of generating the profile, the profile stored in the non-volatile memory 103 can be also updated by operating the operation buttons of the operation panel section 4 in accordance with the display contents of the display unit 3. The drug library having information of the updated profile recorded therein is stored in the non-volatile memory 103 by a method using the communication port 140 and the computer 141 as described above, and thus, the profile stored in the non-volatile memory 103 can be also updated.

The profile can be selected from the plurality of profiles stored in the non-volatile memory 103 so as to be applied to the syringe pump 1 in accordance with the purpose of use. The profile applied to the syringe pump 1 can be selected by operating the operation buttons of the operation panel section 4 in accordance with the display contents of the display unit 3.

Figure 7A:
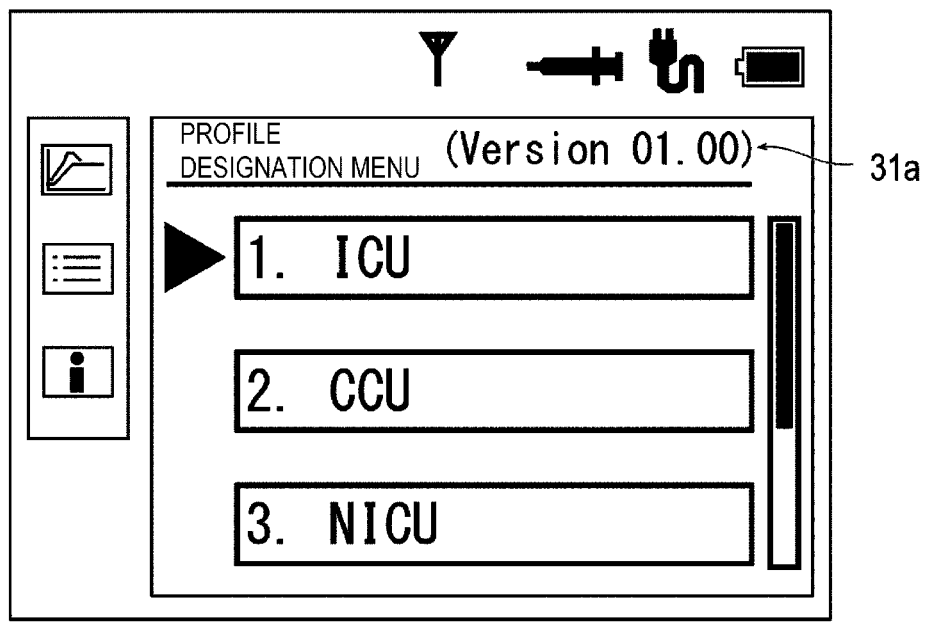
FIGS. 7(A) and 7(B) are other schematic front views for illustrating the display unit of the syringe pump, and the views illustrate display examples when designating a profile.
Figure 7B:
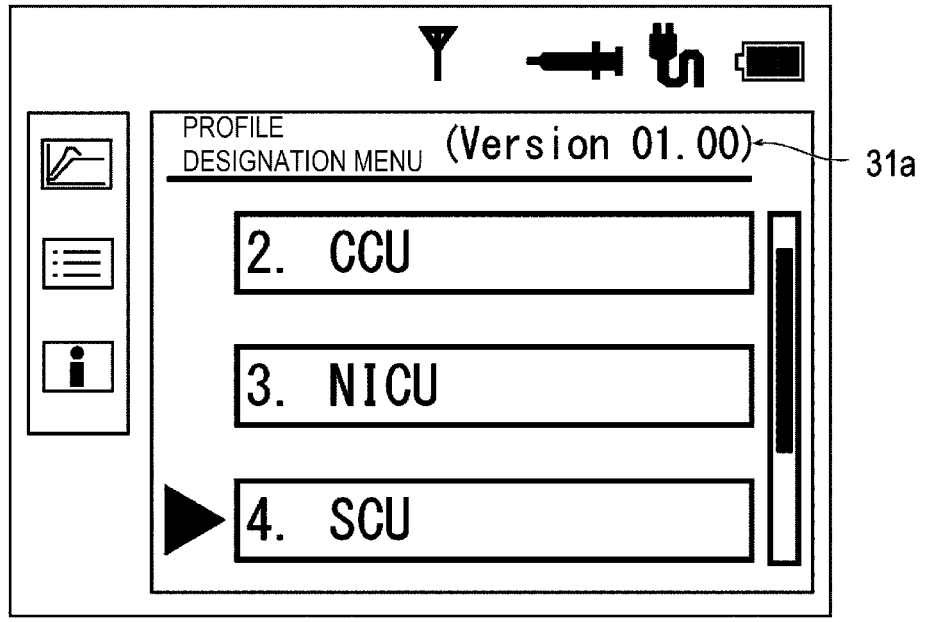

FIGS. 7(A) and 7(B) illustrate examples of the display contents of the display unit 3 at the time of selecting the profile to be applied to the syringe pump 1. As illustrated in FIGS. 7(A) and 7(B), the display unit 3 exhibits a scroll-type display of the names set in the profile which are stored in the non-volatile memory 103. The operation buttons of the operation panel section 4 are operated in accordance with the examples of the display contents illustrated in FIGS. 7(A) and 7(B), and thus, it is possible to select the profile to be applied.

The non-volatile memory 103 stores information which specifies a profile selected as the profile to be applied to the syringe pump 1.

The display unit 3 displays a reception screen 40 for receiving selection of the type of drug which fills the syringe main body 201 set to the syringe setting portion 6. The operation buttons of the operation panel section 4 are operated in accordance with the display contents of the display unit 3, and thus, the type of drug which fills the syringe main body 201 can be input to the control unit 100.

Figure 8A:
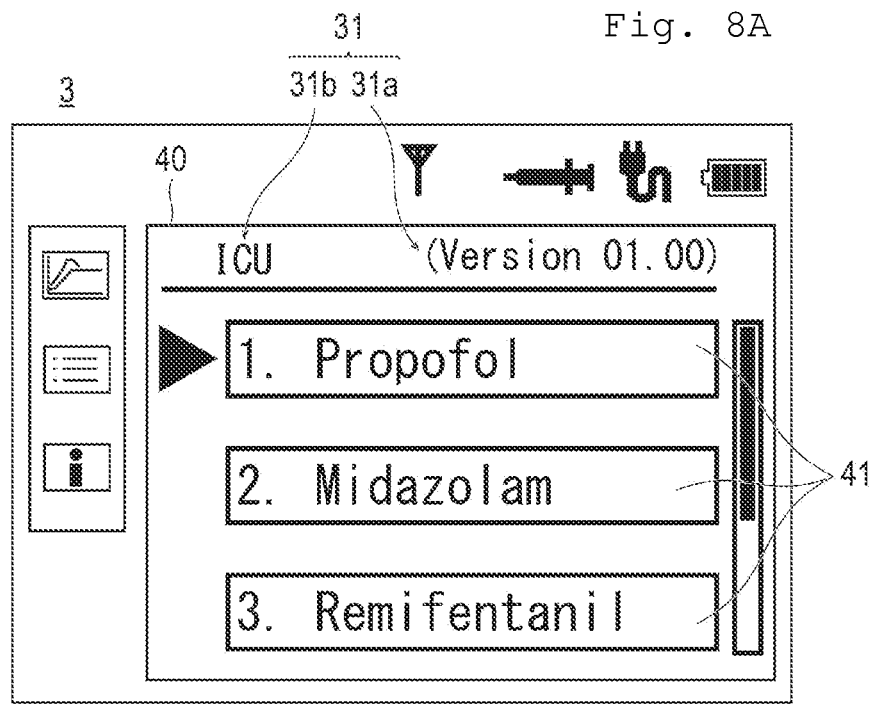
FIGS. 8(A) and 8(B) are other schematic front views for illustrating the display unit of the syringe pump, and the views illustrate display examples when selecting a type of drug to be delivered.
Figure 8B:
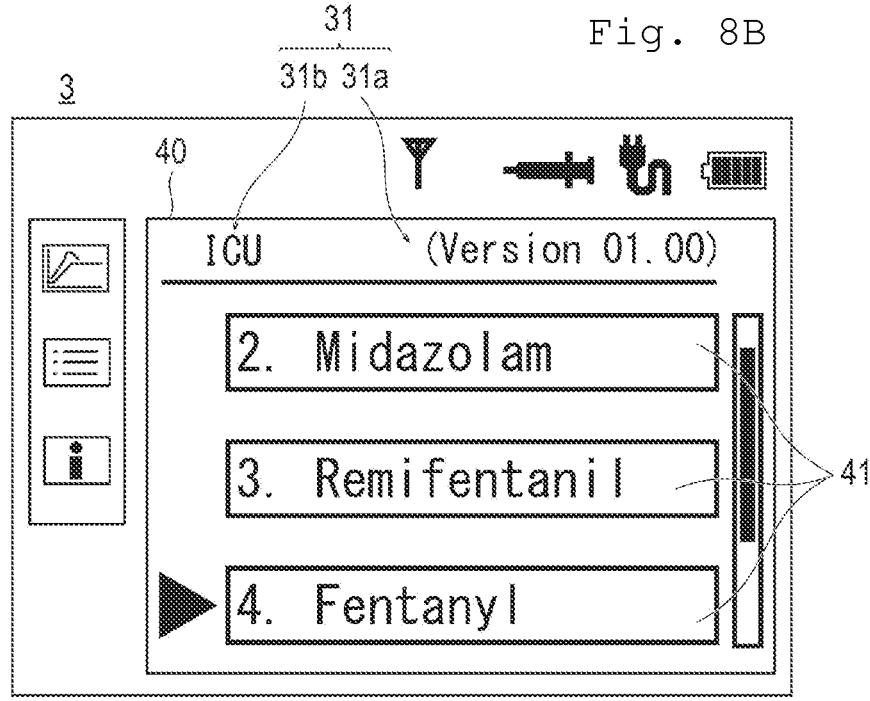

FIGS. 8(A) and 8(B) illustrate examples of the display contents of the display unit 3 at the time of displaying the reception screen 40 for receiving selection of the type of drug which fills the syringe main body 201. On the reception screen 40 for receiving selection of the type of drug, the display unit 3 displays a list 41 of the types of drug(s) which is generated by narrowing the types of drug recorded in the drug library, based on the profile selected as the profile to be applied. Accordingly, it is possible to promptly select the type of drug to be delivered and to input the selection to the control unit 100 in accordance with the purpose of use.

There is a need to input information of the patient P such as gender, age, height, and weight in order to cause the control unit 100 to deliver liquid in accordance with the various parameters with reference to the information of the drug library stored in the non-volatile memory 103. The aforementioned information can be also input by operating the operation buttons of the operation panel section 4 in accordance with the display contents of the display unit 3.

The syringe pump 1 has three starting states such as a liquid deliverable state S1, a power-OFF state S2, and the standby state S3. The liquid deliverable state S1 denotes a starting state where all operations related to delivering of a drug can be performed. The power-OFF state S2 denotes a state where no operation is accepted excluding pressing of the power ON/OFF button 4F. The standby state S3 denotes a state where the rechargeable battery 113 is charged through a power source supplied from the power source converter 112, while in a state where no operation is accepted excluding pressing of the power ON/OFF button 4F.

Figure 9:
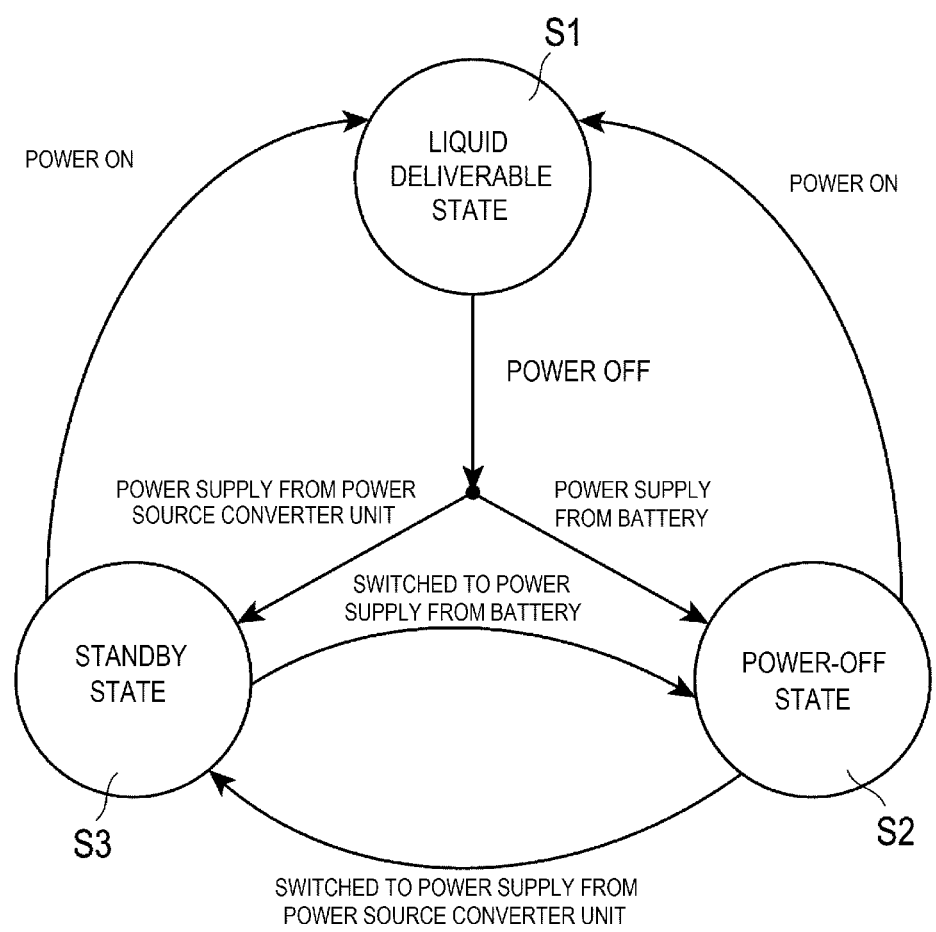
FIG. 9 is a state transition diagram of the syringe pump, and the diagram illustrates state transitions of a starting state thereof.

FIG. 9 is a state transition diagram related to the starting states of the syringe pump 1.

As illustrated in FIG. 9, in a case where a power source is turned OFF while in the liquid deliverable state S1, the starting state transfers to the power-OFF state S2 when the rechargeable battery 113 supplies a power source to the control unit 100, and the starting state transfers to the standby state S3 when the power source converter 112 supplies a power source to the control unit 100. Meanwhile, in a case where the power ON/OFF button 4F is pressed so that a power source is turned ON while in the power-OFF state S2 or the standby state S3, the starting state transfers to the liquid deliverable state S1. In a case where power supply, with respect to the control unit 100, is switched from the rechargeable battery 113 to the power source converter 112 while in the power-OFF state S2, the starting state transfers to the standby state S3. In a case where power supply, with respect to the control unit 100, is switched from the power source converter 112 to the rechargeable battery 113 while in the standby state S3, the starting state transfers to the power-OFF state S2. Turning ON and OFF of a power source is operated by pressing the power ON/OFF button 4F. The power supply with respect to the control unit 100 is switched by the switch 111.

The control unit 100 executes minimal functions necessary to transfer to the liquid deliverable state S1, while in the power-OFF state S2 or the standby state S3. The functions executed by the control unit 100 while in the power-OFF state S2 and the standby state S3 include at least a reception of pressing of the power ON/OFF button 4F and a reception of notification of acceleration measured by the acceleration sensor 160.

The syringe pump 1 is kept in an ME (medical engineer) room and the like when not in use for liquid deliver. The syringe pump 1 is in the standby state S3 while kept in the ME room so as to be able to be promptly used when necessary. When using the syringe pump 1, there is a need to check whether or not the syringe pump 1 is a suitable pump for use before being carried to a site used for delivering liquid. At least, it is necessary to check whether or not the drug library stored in the non-volatile memory 103 is suitable for use.

The display unit 3 displays specification information 31, which specifies a drug library stored in the non-volatile memory 103, while in the standby state S3.

In embodiments, the specification information 31 which specifies a drug library is configured to include updated identification information 31a of the drug library and information 31b which specifies an applied profile applied to the syringe pump 1. However, the embodiments are not limited thereto. The specification information 31, which specifies a drug library, can vary depending on objects. Arbitrary information can be used as the specification information 31 as long as the information can be used for discriminating whether or not the pump is suitable for use. For example, a library name may be set, to the drug, library as the unique name, thereby using the library name as the specification information 31, which specifies a drug library.

In embodiments, the updated identification information 31a, of the drug library, is caused to use a version number, which is applied to the drug library in accordance with the time when the drug library is generated or updated. However, the embodiments are not limited thereto. Arbitrary information can be used as the updated identification information 31a of the drug library as long as it can be determined whether the drug library stored in the non-volatile memory 103 is appropriately updated.

In embodiments, a profile name is used which is set to the applied profile, as the information 31b which specifies an applied profile. However, the embodiments are not limited thereto. Arbitrary information can be used as the information 31b which specifies an applied profile as long as the information is the information which specifies the profile applied to the syringe pump 1.

Figure 10:
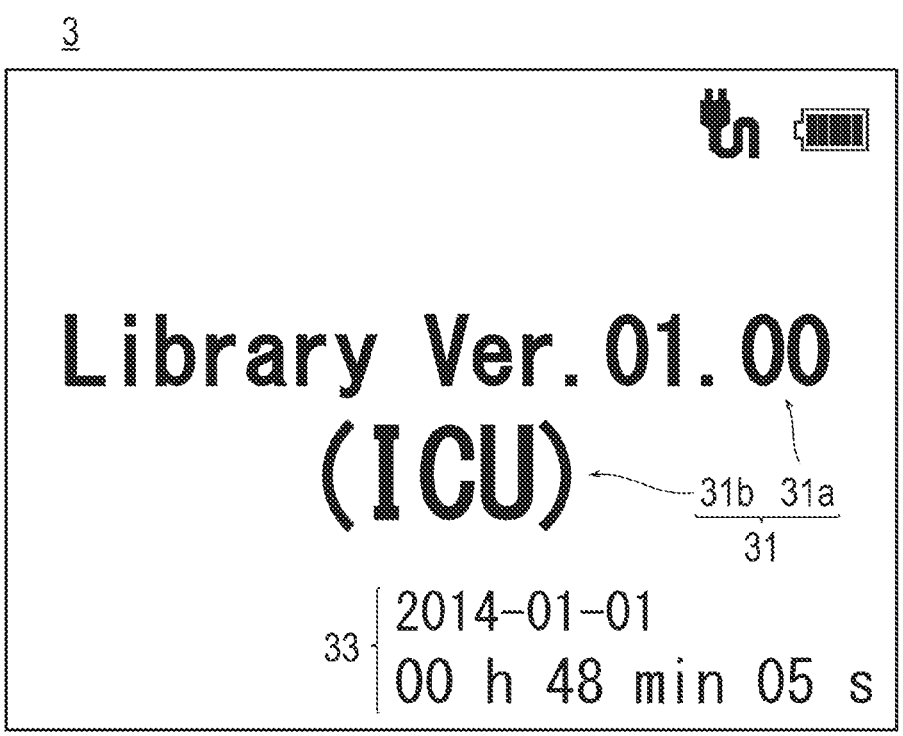
FIG. 10 is another schematic front view for illustrating the display unit of the syringe pump, and the view illustrates a display example when displaying specification information which specifies a drug library including updated identification information of the drug library and information which specifies an applied profile, while in a standby state.

FIG. 10 illustrates an example of the display contents of the display unit 3 at the time of displaying the specification information 31, which specifies a drug library, including the updated identification information 31a of the drug library and the information 31b which specifies an applied profile while in the standby state S3.

As the display unit 3 displays the specification information 31 which specifies a drug library while in the standby state S3, it is possible to judge whether or not a pump is suitable for use while in the standby state S3. Therefore, the syringe pump 1 can be efficiently managed and utilized in the ME room and the like without relying on a complicated method such as attaching of a label.

As the specification information 31, which specifies a drug library, includes the updated identification information 31a of the drug library, it is possible to determine whether the drug library stored in the non-volatile memory 103 is appropriately updated while in the standby state S3. As a result, it is possible to determine whether the syringe pump 1 can deliver liquid while in the standby state S3 based on appropriate information, thereby improving convenience. Specifically, if the drug library stored in the non-volatile memory 103 is not appropriately updated, various parameters such as a proper value or an upper limit value for a flow rate of liquid to be delivered or a proper value or an upper limit value for an infusion rate of drug may be erroneously set. To prevent such erroneous settings, there is a need to check whether the drug library is appropriately updated before the syringe pump 1 is carried from the ME room to a site used for delivering liquid. In the syringe pump 1, the specification information 31 includes the updated identification information 31a of the drug library. The updated identification information 31a of the drug library is information through which a user can determine whether the drug library is appropriately updated. Therefore, in the syringe pump 1, it is possible to determine whether or not the drug library stored in the non-volatile memory 103 is appropriately updated while in the standby state S3. As a result, it is possible to determine whether the syringe pump 1 can deliver liquid, while in the standby state S3 based on appropriate information, thereby improving convenience.

As the specification information 31 which specifies a drug library includes the information 31b which specifies an applied profile, it is possible to determine whether information of drug suitability for use is recorded in the drug library which is stored in the non-volatile memory 103, while in the standby state S3. Moreover, as the specification information 31, which specifies a drug library, includes the information 31b which specifies an applied profile, it is also possible to simultaneously determine whether the types of drug(s) suitable for use can be promptly selected by the syringe pump 1, while in the standby state S3, thereby further improving convenience. Specifically, the profile is a file having a result recorded therein in which the types of drug(s) recorded in the drug library are narrowed in accordance with the purpose of use. In other words, by checking the information 31b which specifies an applied profile, it is possible to determine whether information of drug suitability for use is recorded in the drug library which is stored in the non-volatile memory 103. When selecting a type of drug suitable for use, on the reception screen 40 for receiving selection of the type of drug, the display unit 3 displays the list 41 of the types of drug which is generated by narrowing the types of drug(s) recorded in the drug library, based on the applied profile. Accordingly, it is possible to promptly select the type of drug to be delivered, in accordance with the purpose of use. In other words, by checking the information 31b which specifies an applied profile, it is possible to determine whether the type of drug suitable for use can be promptly selected by the syringe pump 1, while in the standby state S3, thereby further improving convenience.

The display unit 3 includes a power mode switching unit, which switches a power mode between a normal power mode and an energy-saving power mode in which less power is consumed than the normal power mode and information is displayed so as to be visually recognizable when displaying the information, while in the standby state S3.

The power mode switching unit switches the power mode from the normal power mode to the energy-saving power mode when no operation is performed with respect to the syringe pump 1 for a predetermined time while in the normal power mode. The power mode switching unit switches the power mode from the energy-saving power mode to the normal power mode when buttons other than the power ON/OFF button 4F are pressed while in the energy-saving power mode.

As a method of displaying information in a visually recognizable manner while consuming less power than the normal power mode while in the energy-saving power mode, a method of lowering luminance of the display unit 3 can be exemplified.

Figure 11:
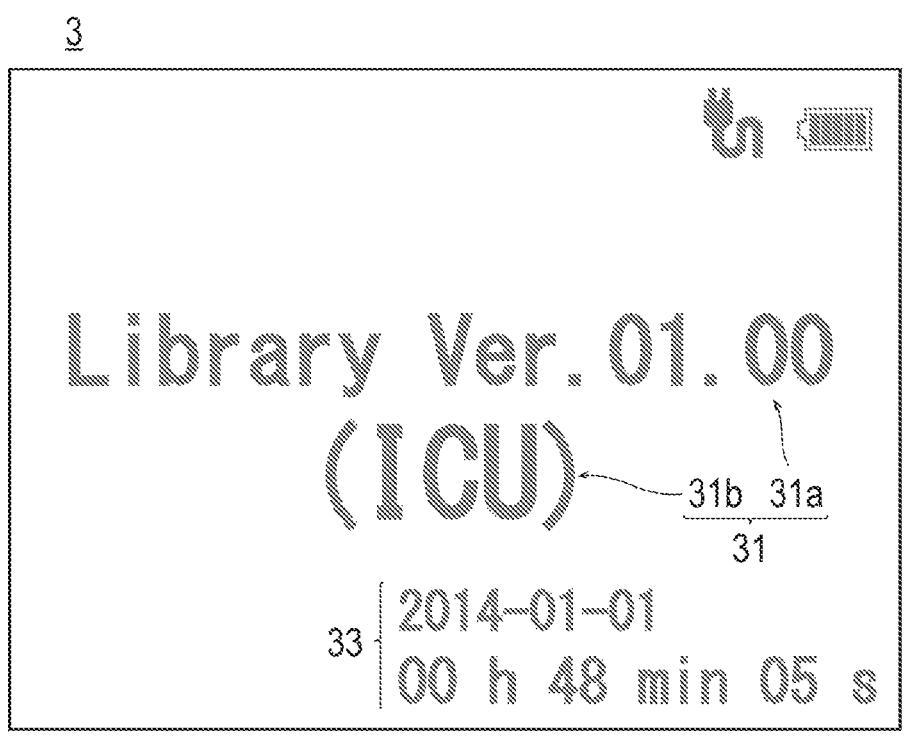
FIG. 11 is another schematic front view for illustrating the display unit of the syringe pump, and the view illustrates a display example when displaying the specification information which specifies a drug library including the updated identification information of the drug library and the information which specifies an applied profile, while in an energy-saving power mode.

FIG. 11 illustrates an example of the display contents of the display unit 3 when the specification information 31 which specifies a drug library including the updated identification information 31a of the drug library and the information 31b which specifies an applied profile is displayed in low luminance.

When the display unit 3 switches the power mode, power consumption is decreased when displaying information necessary to determine whether the pump is suitable for use while in the standby state S3, and thus, a pump can be efficiently managed and utilized.

As illustrated in FIGS. 10 and 11, the display unit 3 may display information 33 of the calendar when displaying the specification information 31 which specifies a drug library stored in the non-volatile memory 103. The display unit 3 can display information related to a current time as the information 33 of the calendar.

In general, the medical pump is periodically inspected. In periodic inspection, consumable components are replaced in accordance with a result of checking whether there is abnormality in operations of the medical pump, or utilization time. When abnormality is found in operations, replacement or repair service of the component is performed. If periodic inspection is not appropriately performed, there may be a disadvantage, such as an occurrence of malfunction during liquid delivery, leading to a stop of liquid delivering.

Therefore, the non-volatile memory 103 functions as the storage unit which stores a periodic inspection time. The display unit 3 displays information 34 which notifies a user of an arrival state of the periodic inspection time, while in the standby state S3.

Judging of an arrival state of the periodic inspection time can be performed by the control unit 100 as described below, for example. In other words, it is possible to judge the arrival state by comparing a current time acquired from the clock 104 and the periodic inspection time stored in the non-volatile memory 103.

Figure 12A:
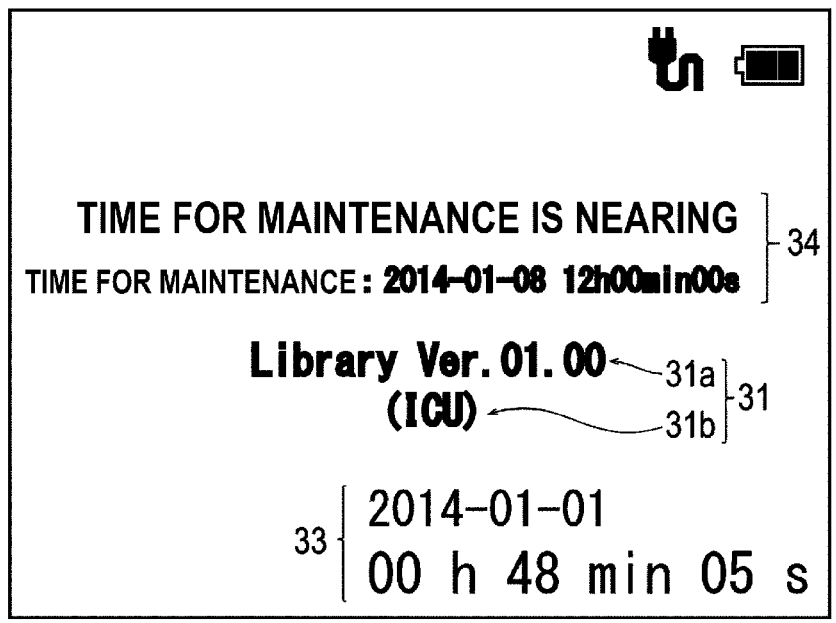
FIGS. 12(A) and 12(B) are other schematic front views for illustrating the display unit of the syringe pump, and the views illustrate display examples when displaying information which notifies a user of an arrival state of a periodical inspection time.
Figure 12B:
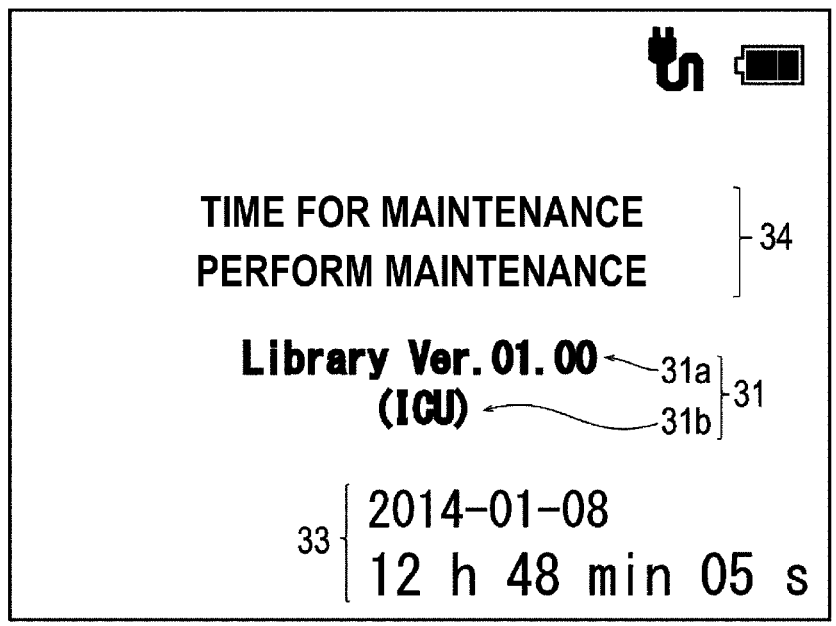

FIGS. 12(A) and 12(B) illustrate examples of the display contents of the display unit 3 when displaying an arrival state of the periodic inspection time.

As the information 34, which notifies a user of an arrival state of the periodic inspection time, FIG. 12(A) illustrates the example of the display contents when displaying information notifying that the periodic inspection time is nearing.

As the information 34, which notifies a user of an arrival state of the periodic inspection time, FIG. 12(B) illustrates the example of the display contents when displaying information notifying that the current time has passed the periodic inspection time.

As illustrated in FIGS. 12(A) and 12(B), the display unit 3 may display the specification information 31 which specifies a drug library including the updated identification information 31a of the drug library and the information 31b which specifies an applied profile together with the information 34 which notifies a user of an arrival state of the periodic inspection time.

The periodic inspection time stored in the non-volatile memory 103 can be appropriately set by a health care worker who manages the syringe pump 1. It is also possible to appropriately set the time for displaying the information notifying that the periodic inspection time is nearing. For example, the time may be set to display the information when the period from the current time to the periodic inspection time is less than one week, or may be set to display the information when the period is less than two weeks.

As the display unit 3 displays the information 34 which notifies a user of an arrival state of the periodic inspection time, while in the standby state S3, it is possible to determine whether periodic inspection is appropriately performed, while in the standby state S3.

The medical pump needs to precisely deliver a drug in accordance with the various parameters prescribed for each type of drug. Accordingly, components used in the medical pump may include a highly precise component, which may break down or be damaged by an external shock. In a case of break-down or damage occurring in the component, there may be a disadvantage that liquid delivering is not precisely performed in accordance with the various parameters prescribed for each type of drug.

In medical pumps of the related art, there is a pump which detects an external shock and stores the history of shocks applied. However, in the medical pumps of the related art, checking whether or not a shock is applied can be performed in only the liquid deliverable state S1. Therefore, if the pump is kept in the ME room and the like while in the standby state S3, it is not possible to promptly check whether or not a shock is applied.

Therefore, the acceleration sensor 160 functions as a shock detection unit which detects whether a shock is applied to the syringe pump 1. The display unit 3 displays information 35 which notifies a user of whether a shock is detected by the acceleration sensor 160, while in the standby state S3.

As described above, the control unit 100 receives notification of acceleration measured by the acceleration sensor 160 in all starting states. In other words, the control unit 100 can detect a shock not only in the liquid deliverable state S1 but also in the power-OFF state S2 and the standby state S3.

Figure 13:
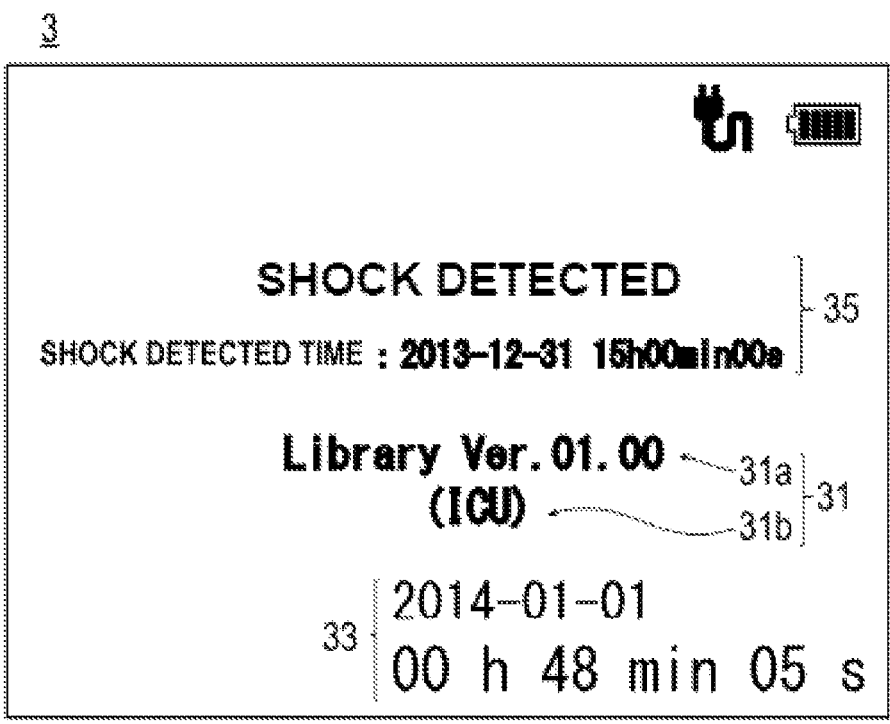
FIG. 13 is another schematic front view for illustrating the display unit of the syringe pump, and the view illustrates a display example when displaying information which notifies a user of whether or not a shock is detected.

FIG. 13 illustrates an example of the display contents of the display unit 3 when displaying the information 35 which notifies a user that a shock is detected by the acceleration sensor 160, while in the standby state S3.

As the display unit 3 displays the information 35 which notifies a user that a shock is detected by the acceleration sensor 160, while in the standby state S3, it is possible to discriminate whether a shock is detected, while in the standby state S3.

Moreover, the display unit 3 may display information which notifies a user that a shock is detected by the acceleration sensor 160, while in the power-OFF state S2 as well.

As illustrated in FIG. 13, the display unit 3 may display the specification information 31 which specifies a drug library including the updated identification information 31a of the drug library and the information 31b which specifies an applied profile together with the information 35 which notifies a user that a shock is detected.

The display unit 3 may display the specification information 31 which specifies a drug library on the reception screen 40 which receives selection of the type of drug which fills the syringe main body 201.

FIGS. 8(A) and 8(B) illustrate an example of the display contents of the display unit 3 when displaying the specification information 31 which specifies a drug library including the updated identification information 31a of the drug library and the information 31b which specifies an applied profile on the reception screen 40 which receives selection of the type of drug which fills the syringe main body 201.

As the specification information 31, which specifies a drug library, is displayed on the reception screen 40, it is possible to prevent a pump not suitable for use from being used, thereby improving safety.

As described above, if the drug library stored in the non-volatile memory 103 is not appropriately updated, various parameters such as a proper value or an upper limit value for a flow rate of liquid to be delivered or a proper value or an upper limit value for an infusion rate of drug may be erroneously set. As the specification information 31 displayed on the reception screen 40 includes the updated identification information 31a of the drug library, it is possible to prevent the various parameters from being erroneously set.

If an applied profile is not suitable for use, the list 41 of the types of drug(s) not suitable for use is displayed on the reception screen 40 which receives selection of the types of drug. Since some types of drug(s) have names similar to one another and the list 41 of the types of drug(s) not suitable for use is displayed, a possibility to erroneously select the type of drug to be delivered increases. As the specification information 31 displayed on the reception screen 40 includes the information 31b which specifies an applied profile, it is possible to prevent such erroneous selection.

Subsequently, an example of use of the syringe pump 1 will be described.

Firstly, preparatory work is performed in the ME room in the following procedure.

The power ON/OFF button 4F is pressed so as to be in the liquid deliverable state S1.

Subsequently, as illustrated in FIG. 5, the control unit 100 and the computer 141 are connected to each other through the communication port 140.

Subsequently, the computer 141 is operated, and a drug library including information of the plurality of profiles is input to the control unit 100 from the drug database 150 through the communication port 140. Through the aforementioned operation, the drug library and the plurality of profiles recorded in the drug library are stored in the non-volatile memory 103.

Subsequently, the operation buttons of the operation panel section 4 are operated in accordance with the display contents of the display unit 3 as described in FIG. 7, thereby selecting the profile to be applied in accordance with the purpose of use.

Subsequently, the power ON/OFF button 4F is pressed so as to turn the power source OFF.

Subsequently, the syringe pump 1 is moved to a suitable keeping place in the ME room.

Subsequently, the power plug 114 is connected to the commercial AC power source 115 installed in the keeping place. In this case, as illustrated in FIG. 9, the syringe pump 1 is in the standby state S3.

According to the procedure described above, the prior preparatory work is completed. As necessary, a plurality of the syringe pumps 1 are subjected to the above-described prior preparation.

Subsequently, a case of carrying the syringe pump 1 from the ME room to a site used for delivering liquid will be described.

The syringe pump 1 is carried to a site used for delivering a drug upon request from a site such as the intensive care unit (ICU) and the like. In this case, there is a need to select a syringe pump 1 suitable for use out of the plurality of syringe pumps 1 kept in the ME room so as to be carried to the site.

Selection of the syringe pump 1 suitable for use is performed in accordance with the information displayed on the display unit 3.

As illustrated in FIGS. 10 and 11, the display unit 3 displays the specification information 31 which specifies a drug library including the updated identification information 31a of the drug library and the information 31b which specifies an applied profile, while in the standby state S3, and in the normal power mode or the energy-saving power mode.

It is possible to promptly select the syringe pump 1 suitable for use out of the plurality of syringe pumps 1 by checking the specification information 31 which specifies a drug library including the updated identification information 31a of the drug library and the information 31b which specifies an applied profile displayed on the display unit 3.

As illustrated in FIGS. 12(A) and 12(B), the display unit 3 displays the information 34 which notifies a user of an arrival state of the periodical inspection time in accordance with the arrival state of the periodic inspection time.

As illustrated in FIG. 13, when the acceleration sensor 160 detects a shock, the display unit 3 displays the information 35 which notifies a user that a shock is applied.

Whether the pump can be used for delivering liquid is checked from the information displayed on the display unit 3. As the display unit 3 displays the information 34 which notifies a user of an arrival state of the periodic inspection time and the information 35 which notifies a user that a shock is applied, while in the standby state S3, it is possible to promptly check whether the pump can be appropriately used for delivering liquid.

After selecting a pump which is suitable for use and can be appropriately used for delivering liquid, the syringe pump 1 is carried to a site used for delivering liquid.

Subsequently, a procedure, after being carried to a site used for delivering liquid, will be described.

Firstly, as illustrated in FIGS. 1 and 2, the syringe 200 is coupled to the syringe pump 1. The syringe pump 1 is coupled by the above-described method using the clamp 5.

Subsequently, the type of drug which fills the syringe main body 201 is selected by operating the operation buttons of the operation panel section 4 in accordance with the display contents of the reception screen 40 which is displayed on the display unit 3 as illustrated in FIG. 8.

In this case, as illustrated in FIG. 8, the specification information 31 which specifies a drug library including the updated identification information 31a of the drug library and the information 31b which specifies an applied profile is displayed on the display unit 3. The displayed information is checked whether the drug library stored in the non-volatile memory 103 and the applied profile are suitable for use. If the drug library and the applied profile are not suitable for use, it is judged whether the process is continued in consideration of urgency. If the process is not continued, another syringe pump 1 suitable for use is carried from the ME room, thereby restarting the process.

Subsequently, the indwelling needle 204 having the tube 203 connected thereto is inserted into the patient P.

Subsequently, the operation buttons of the operation panel section 4 are operated in accordance with the display contents of the display unit 3, thereby inputting gender, age, height, and weight or the like as information of the patient P.

Subsequently, the start switch button 4C is pressed to start delivering the drug to the inside of the patient P. Delivery of the drug is performed in accordance with various parameters recorded in the drug library stored in the non-volatile memory 103 and in accordance with the type of selected drug.

After delivering drug is completed, the syringe pump 1 is returned to and kept in the ME room for the next use.

According to embodiments, the information 31 which specifies a drug library stored in the non-volatile memory 103 is displayed on the display unit 3, while in the standby state S3. Accordingly, it is possible to determine whether a pump is suitable for use, while in the standby state S3. Therefore, it is possible to provide a liquid delivering pump which can be efficiently managed and utilized.

According to embodiments, the specification information 31 which specifies a drug library includes the updated identification information 31a of the drug library. Therefore, it is possible to determine whether the drug library stored in the non-volatile memory 103 is appropriately updated, while in the standby state S3. Thus, it is possible to determine whether the pump can deliver liquid, while in the standby state S3 based on appropriate information, thereby improving convenience.

The specification information 31 which specifies a drug library includes information which specifies the profile applied to the syringe pump 1. Therefore, it is possible to determine whether information of drug suitable for use is recorded in the drug library stored in the non-volatile memory 103, while in the standby state S3. Moreover, it is also possible to determine whether the type of drug suitable for use can be promptly selected by the pump, while in the standby state S3, thereby further improving convenience.

The non-volatile memory 103 stores the periodic inspection time. The display unit 3 displays the information 34 which notifies a user of an arrival state of the periodical inspection time, while in the standby state S3. Accordingly, it is possible to determine whether the periodical inspection is appropriately performed, while in the standby state S3. Thus, a pump can be more efficiently managed and utilized.

The acceleration sensor 160 functions as the shock detection unit which detects whether the pump is subjected to a shock. The display unit 3 displays the information 35 which notifies a user of whether or not a shock is detected, while in the standby state S3. Accordingly, it is possible to determine whether a shock is detected, while in the standby state S3. Thus, a pump can be further efficiently managed and utilized.

The display unit 3 includes the power mode switching unit which switches the power mode between the normal power mode and the energy-saving power mode in which less power is consumed than the normal power mode and the specification information 31 is displayed so as to be visually recognizable when displaying the specification information 31 which specifies a drug library, while in the standby state S3. The power mode switching unit switches the power mode from the normal power mode to the energy-saving power mode when no operation is performed with respect to the syringe pump 1 for a predetermined time while in the normal power mode. Accordingly, it is possible to decrease power consumption when displaying information necessary to determine whether the pump is suitable for use, while in the standby state S3. Thus, a pump can be more efficiently managed and utilized.

The display unit 3 displays the reception screen 40 which receives selection of the type of drug to be delivered, while in the liquid deliverable state S1. The display unit 3 also displays the specification information 31 which specifies a drug library on the reception screen 40. Accordingly, when selecting a type of drug to be delivered, while in the liquid deliverable state S1, it is possible to determine whether the pump is suitable for use. Therefore, it is possible to prevent a pump not suitable for use from being used, thereby improving safety.

Modification Example 1

In the above-described embodiments, the display unit 3 displays the profile name set in the applied profile as the information 31b which specifies the applied profile. However, the embodiments are not limited thereto. As described above, as long as it is possible to determine whether the profile suitable for use is applied to the syringe pump 1, arbitrary information can be used as the information 31b which specifies the profile.

For example, the profile IDs may be respectively set so as to cause the plurality of the profiles stored in the non-volatile memory 103 to be identifiable, and a visually identifiable icon 36 may be displayed replacing the profile ID.

Figure 14:
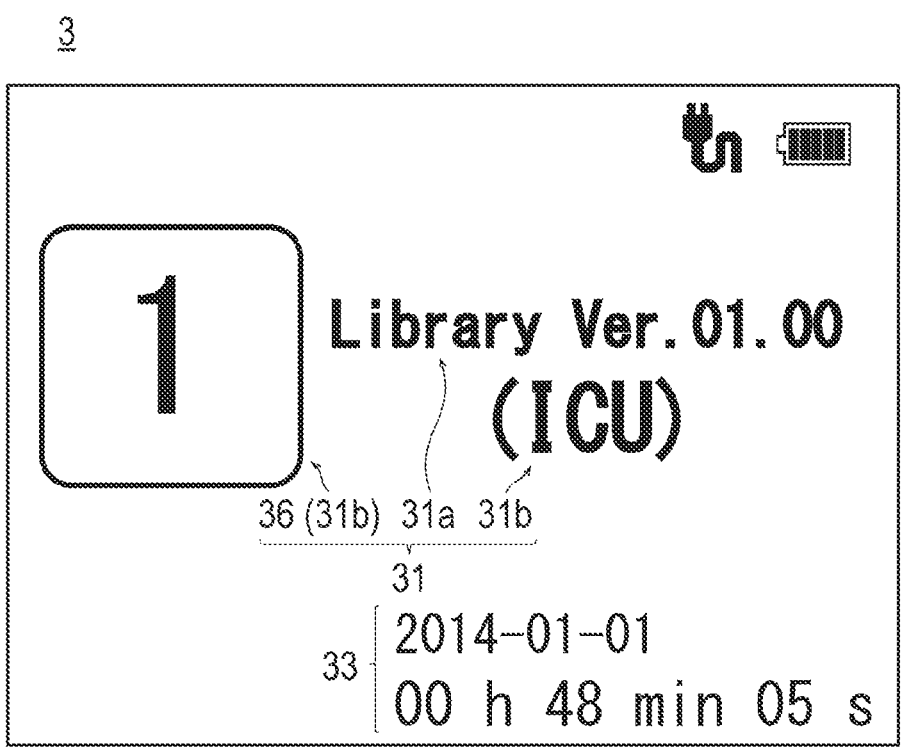
FIG. 14 is a schematic front view for illustrating the display unit of the syringe pump in a modification example, and the view illustrates a display example when displaying an icon replacing the information which specifies an applied profile.

FIG. 14 illustrates an example of the display contents of the display unit 3 when the profile ID is replaced by the icon 36 and the information 31b which specifies an applied profile is displayed.

As illustrated in FIG. 14, the updated identification information 31a of the drug library may be simultaneously displayed when the information 31b which specifies the applied profile is replaced by the icon 36 and displayed thereon. As illustrated in FIG. 14, the profile name set to the applied profile may be simultaneously displayed together with the icon 36, as the information 31b which specifies the applied profile.

The example of the display contents illustrated in FIG. 14 indicates a case where serial numbers are set as the profile ID. However, the embodiments are not limited thereto. As long as each of the plurality of the profiles stored in the non-volatile memory 103 is identifiable, arbitrary signs or information can be used as the profile ID. For example, numerals, alphabets, and other signs can be used as the profile ID.

By configuring the display unit 3 as described above, it is possible to visually determine whether the pump is suitable for use. Therefore, time taken for determination is decreased, thereby improving convenience and preventing erroneous identification at the time of discrimination, leading to an improvement of safety.

Modification Example 2

The display unit 3 may vary a display state at the time of displaying the specification information 31 which specifies a drug library stored in the non-volatile memory 103 in accordance with the applied profile.

Figure 15A:
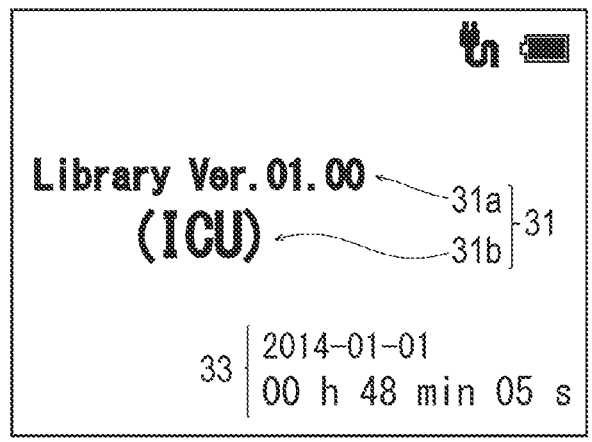
FIGS. 15(A) to 15(C) are other schematic front views for illustrating the display unit of the syringe pump in a modification example, and the views illustrate display examples when varying a display position of the specification information which specifies a drug library including the updated identification information of the drug library and the information which specifies an applied profile in accordance with the applied profile.
Figure 15B:
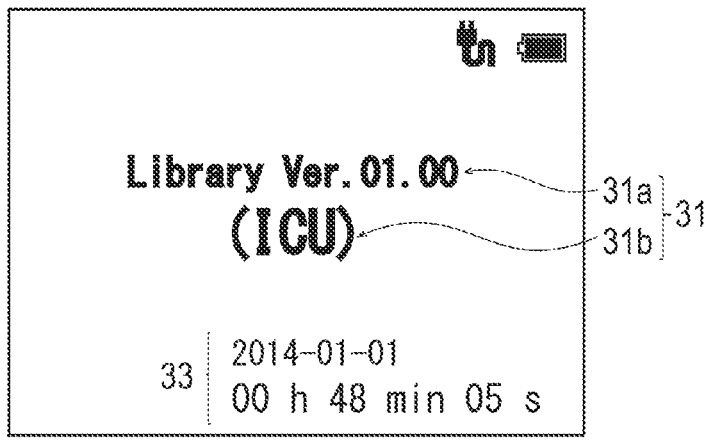
Figure 15C:
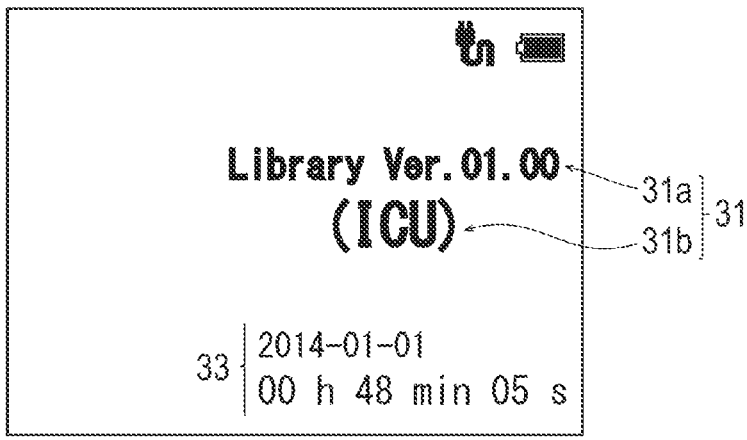

FIGS. 15(A) to 15(C) illustrate examples of the display contents of the display unit 3 when varying a display position at the time of displaying the specification information 31 which specifies a drug library including the updated identification information 31a of the drug library and the information 31b which specifies an applied profile, in accordance with the applied profile.

In the examples of the display contents illustrated in FIG. 15, serial numbers are set to the plurality of profiles stored in the non-volatile memory 103 as the profile IDs causing each profile to be identifiable. FIG. 15(A) illustrates an example of the display contents in a case where the remainder is 1 when the number of the profile IDs of the applied profiles is divided by 3. FIG. 15(B) illustrates an example of the display contents in a case where the remainder is 2 when the number of the profile IDs of the applied profiles is divided by 3. FIG. 15(C) illustrates an example of the display contents in a case where the remainder is zero when the number of the profile IDs of the applied profiles is divided by 3.

In the examples of the display contents illustrated in FIGS. 15(A) to 15(C), the display position of the specification information 31 which specifies a drug library including the updated identification information 31a of the drug library and the information 31b which specifies an applied profile is varied respectively to the left end, to the center, and to the right end in the display unit 3. However, the embodiments are not limited thereto. For example, the position may be varied to the top, to the center, and to the bottom in the display unit 3 in accordance with the applied profile.

In the examples of the display contents illustrated in FIG. 15, regarding the display position of the specification information 31 which specifies a drug library including the updated identification information 31a of the drug library and the information 31b which specifies an applied profile, the display position is varied in accordance with the applied profile. However the embodiments are not limited thereto. The color and size at the time of displaying the specification information 31 which specifies a drug library stored in the non-volatile memory 103 may be varied.

By configuring the display unit 3 as described above, it is possible to easily identify the applied profile. Therefore, it is possible to decrease erroneous identification at the time of determining whether the profile suitable for use is applied, thereby further improving convenience and safety.

Modification Example 3

In the display unit 3, the display state at the time of displaying the specification information 31 which specifies a drug library stored in the non-volatile memory 103 may be varied in accordance with an elapsed time from an update of the drug library.

Figure 16A:
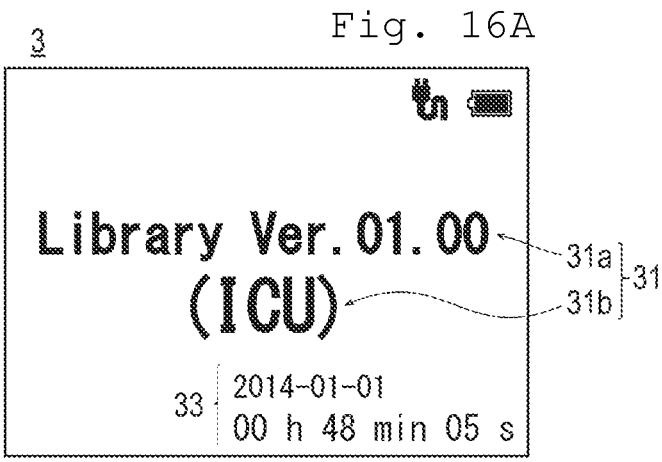
FIGS. 16(A) to 16(C) are other schematic front views for illustrating the display unit of the syringe pump in a modification example, and the views illustrate display examples when varying a display color of the specification information which specifies a drug library including the updated identification information of the drug library and the information which specifies an applied profile in accordance with an elapsed time from an update of the drug library.
Figure 16B:
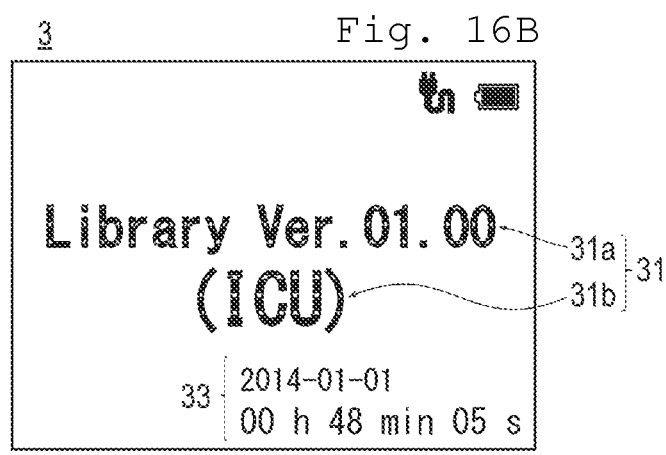
Figure 16C:
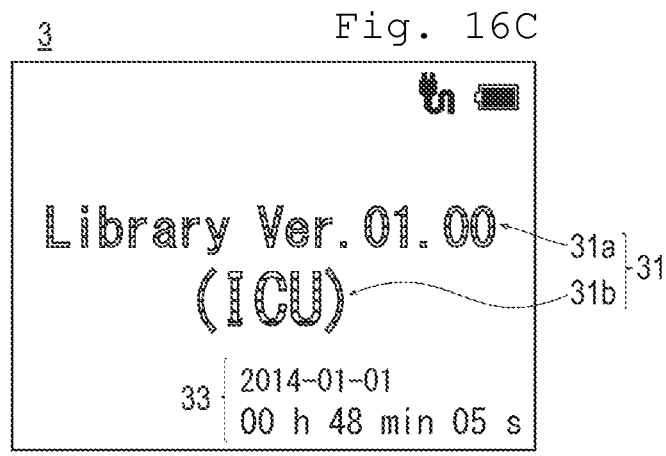

FIGS. 16(A) to 16(C) illustrate examples of the display contents of the display unit 3 when varying a display color at the time of displaying the specification information 31 which specifies a drug library including the updated identification information 31a of the drug library and the information 31b which specifies an applied profile in accordance with an elapsed time from an update of the drug library.

FIG. 16(A) illustrates an example of the display contents in a case where the elapsed time from an update of the drug library is within one day. FIG. 16(B) illustrates an example of the display contents in a case where the elapsed time from an update of the drug library ranges from one day to one week. FIG. 16(C) illustrates an example of the display contents in a case where the elapsed time from an update of the drug library is equal to or exceeding one week.

In the examples of the display contents illustrated in FIG. 16, regarding the display color at the time of displaying the specification information 31 which specifies a drug library including the updated identification information 31a of the drug library and the information 31b which specifies an applied profile, the display color is caused to fade in the order of those in FIG. 16(A), FIG. 16(B), and FIG. 16(C). However, the embodiments are not limited thereto. The display color may be caused to be darker in the order of those displays in FIG. 16(A), FIG. 16(B), and FIG. 16(C). Otherwise, the display color may be varied to different colors such as red, green, black, and the like.

In the examples of the display contents illustrated in FIG. 16, the display colors of both the updated identification information 31a of the drug library and the information 31b which specifies an applied profile are varied. However, either one of the display colors may be varied.

Moreover, in the examples of the display contents in FIG. 16, the display colors of the specification information 31 which specifies a drug library is varied by dividing the elapsed time from an update of the drug library into three terms. However, the terms to be varied in display color can be arbitrarily set. For example, the display colors may be varied by dividing the elapsed time from an update of the drug library into two terms such as a term of within one week and a term of equal to or exceeding one week.

In the examples of the display contents in FIG. 16, the display color of the specification information 31 which specifies a drug library is varied in accordance with an elapsed time from an update of the drug library. However, the embodiments are not limited thereto. For example, the display position or size at the time of displaying the specification information 31 which specifies a drug library may be varied. Elapsed days or the elapsed time from an update of the drug library may be displayed numerically.

By configuring the display unit 3 as described above, it is possible to easily identify the elapsed time from an update of the drug library stored in the non-volatile memory 103. Accordingly, it is possible to decrease erroneous identification when determining whether the drug library stored in the non-volatile memory 103 is appropriately updated, thereby further improving convenience and safety.

Hereinbefore, the liquid delivering pump has been described through the embodiments above and each of the modification examples. However, the liquid delivering pump according to the present invention is not limited to only the configurations thereof and it is possible to make various changes and modifications based on the disclosed scope of Claims.

In the embodiment and modification examples described above, a case where the embodiments are applied to a syringe pump has been described. However, the embodiments are not limited thereto. The embodiments can be widely applied to medical liquid delivering pumps such as infusion pumps in which an amount of drug to be delivered can be adjusted.

REFERENCE SIGNS LIST 1 syringe pump,
2 main body cover,
2A upper portion of main body cover,
2B lower portion of main body cover,
3 display unit,
4 operation panel section,
5 clamp,
6 syringe setting portion,
7 syringe plunger drive unit,
8 accommodation portion, 9 tube fixing portion,
31 specification information which specifies drug library,
31a updated identification information of drug library,
31b information which specifies applied profile,
36 icon,
40 reception screen,
100 control unit,
103 non-volatile memory,
160 acceleration sensor,
200, 300, 400 syringe,
201, 301, 401 syringe main body,
202, 302, 402 syringe plunger,
P patient,
S1 liquid deliverable state,
S2 power-OFF state, and
S3 standby state.

What is claimed is:

1. A liquid delivering pump which delivers a drug to an inside of a living body, comprising:
a control unit;
a storage unit that stores a drug library;
a starting state switching unit that switches a starting state of the liquid delivering pump between one of the following states:
   a liquid deliverable state where the liquid delivering pump performs operations related to delivery of a liquid;
   a power-off state where the liquid delivering pump is powered off and is not receiving power from the power source converter, and where no operation is accepted excluding pressing of a power ON/OFF button; and
   a standby state, where the liquid delivering pump is powered off and is receiving power from the power source converter, wherein the standby state is a rechargeable state for recharging a rechargeable battery, and where no operation is accepted excluding pressing of the power ON/OFF button; and
a display unit driven by a display unit driver electrically connected to the control unit;
wherein the display unit displays various types of information related to the liquid delivering pump,
wherein the liquid delivery pump is controlled by the control unit,
wherein, while in the standby state, the display unit displays specification information which specifies the drug library stored in the storage unit, when the liquid delivering pump is plugged into an outlet and when the liquid delivering pump is switched off concurrently with recharging the rechargeable battery, and
wherein the specification information includes identification information for a version of the drug library.

2. The liquid delivering pump according to claim 1, wherein the specification information includes updated identification information of the drug library.

3. The liquid delivering pump according to claim 2, wherein the drug library includes a plurality of profiles, and the specification information includes information which specifies the profile applied to the liquid delivering pump.

4. The liquid delivering pump according to claim 3, wherein profile identifiers (IDs) are respectively set to cause the plurality of profiles to be identifiable, and wherein the display unit displays a visually identifiable icon replacing the profile ID set to the applied profile when displaying the information which specifies the profile applied to the liquid delivering pump in the specification information.

5. The liquid delivering pump according to claim 3, wherein the display unit varies a display state at a time of displaying the specification information in accordance with the applied profile.

6. The liquid delivering pump according to claim 5, wherein the display unit varies the display state at the time of displaying the specification information in accordance with an elapsed time from an update of the drug library.

7. The liquid delivering pump according to claim 5, wherein the storage unit also stores a periodic inspection time, and wherein the display unit displays information which notifies a user of an arrival state of the periodical inspection time, while in the standby state.

8. The liquid delivering pump according to claim 7, further comprising: a shock detection unit that detects whether the liquid delivering pump is subjected to a shock, wherein the display unit displays information which notifies the user of whether the shock is detected by the shock detection unit, while in the standby state.

9. The liquid delivering pump according to claim 8, wherein the display unit includes a power mode switching unit which switches a power mode between a normal power mode and an energy-saving power mode, in which less power is consumed than the normal power mode, and wherein the power mode switching unit switches the power mode from the normal power mode to the energy-saving power mode when no operation is performed with respect to the liquid delivering pump for a predetermined time, while in the normal power mode.

10. The liquid delivering pump according to claim 9, wherein the display unit displays a reception screen which receives selection of a drug type to be delivered, while in the liquid deliverable state, and displays the specification information on the reception screen.

* * * * *